US008660631B2

(12) United States Patent
Feke et al.

(10) Patent No.: US 8,660,631 B2
(45) Date of Patent: Feb. 25, 2014

(54) TORSIONAL SUPPORT APPARATUS AND METHOD FOR CRANIOCAUDAL ROTATION OF ANIMALS

(75) Inventors: Gilbert Feke, Glastonbury, CT (US); Benjamin F. Geldhof, East Hartford, CT (US); Warren M. Leevy, West Haven, CT (US); Mark E. Bridges, Spencerport, NY (US); William E. McLaughlin, Guilford, CT (US); Rao Papineni, Branford, CT (US)

(73) Assignee: Bruker Biospin Corporation, Billerica, MA (US)

( * ) Notice: Subject to any disclaimer, the term of this patent is extended or adjusted under 35 U.S.C. 154(b) by 490 days.

(21) Appl. No.: 12/475,623

(22) Filed: Jun. 1, 2009

(65) Prior Publication Data
US 2010/0022866 A1    Jan. 28, 2010

Related U.S. Application Data

(63) Continuation-in-part of application No. 11/221,530, filed on Sep. 8, 2005, now Pat. No. 7,734,325, and a continuation-in-part of application No. 12/196,300, filed on Aug. 22, 2008, now abandoned, and a continuation-in-part of application No. 12/354,830, filed on Jan. 16, 2009, now Pat. No. 8,050,735, and a continuation-in-part of application No. 12/381,599, filed on Mar. 13, 2009, and a continuation-in-part of application No. 12/411,432, filed on Mar. 26, 2009, now Pat. No. 8,504,140.

(60) Provisional application No. 61/131,948, filed on Jun. 13, 2008.

(51) Int. Cl.
*A61B 5/05* (2006.01)

(52) U.S. Cl.
USPC .......................................... 600/407; 600/425

(58) Field of Classification Search
USPC .......................... 600/407–429, 437; 128/877
See application file for complete search history.

(56) References Cited

U.S. PATENT DOCUMENTS 1,609,703 A    12/1926 Eggert et al.
3,717,764 A    2/1973 Fujimura et al.
(Continued)

FOREIGN PATENT DOCUMENTS

EP    1 111 625 A2    6/2001
EP    1 304 070 A2    4/2003
(Continued)

OTHER PUBLICATIONS

Pete Mitchell, PharmaDD—Tracking Discovery & Development, Picture Perfect: Imaging Gives Biomarkers New Look, Nov./Dec. 2006, vol. 1, No. 3, pp. 1-5.
(Continued)

*Primary Examiner* — Tse Chen
*Assistant Examiner* — Vani Gupta
(74) *Attorney, Agent, or Firm* — O'Shea Getz P.C.

(57) ABSTRACT

A torsional support apparatus is disclosed for craniocaudal rotation of test animals to enable multiple-view imaging. The animal is supported in a U-shaped loop of optically transparent material and the loop is moved to apply torsion to the animal to rotate it about its craniocaudal axis. Methods of imaging also are disclosed that use the torsional support technique.

25 Claims, 40 Drawing Sheets

(56) References Cited

U.S. PATENT DOCUMENTS

| | | | |
|---|---|---|---|
| 3,936,644 A | 2/1976 | Rabatin | |
| 4,028,550 A | 6/1977 | Weiss et al. | |
| 4,088,894 A | 5/1978 | Rabatin | |
| 4,107,070 A | 8/1978 | Everts et al. | |
| 4,208,470 A | 6/1980 | Rabatin | |
| 4,232,227 A | 11/1980 | Finkenzeller et al. | |
| 4,296,861 A * | 10/1981 | Barrash | 206/428 |
| 4,394,737 A | 7/1983 | Komaki et al. | |
| 4,446,365 A | 5/1984 | Ong et al. | |
| 4,675,529 A | 6/1987 | Kushida | |
| 4,710,637 A | 12/1987 | Luckey et al. | |
| 4,829,188 A | 5/1989 | Shinomiya et al. | |
| 4,870,279 A | 9/1989 | Cueman et al. | |
| 4,891,527 A | 1/1990 | Rabatin | |
| 4,898,175 A | 2/1990 | Noguchi | |
| 5,069,982 A | 12/1991 | Zegarski | |
| 5,307,804 A | 5/1994 | Bonnet | |
| 5,501,225 A | 3/1996 | Wilson | |
| 5,517,193 A | 5/1996 | Allison et al. | |
| 5,534,709 A * | 7/1996 | Yoshimoto et al. | 250/588 |
| 5,650,135 A | 7/1997 | Contag et al. | |
| 5,663,005 A | 9/1997 | Dooms et al. | |
| 5,717,791 A | 2/1998 | Labaere et al. | |
| 5,730,701 A | 3/1998 | Furukawa et al. | |
| 5,748,768 A | 5/1998 | Sivers et al. | |
| 5,830,629 A | 11/1998 | Vizard et al. | |
| 6,227,704 B1 | 5/2001 | Bani-Hashemi et al. | |
| 6,229,873 B1 | 5/2001 | Bani-Hashemi et al. | |
| 6,268,613 B1 | 7/2001 | Cantu et al. | |
| 6,269,177 B1 | 7/2001 | Dewaele et al. | |
| 6,278,765 B1 | 8/2001 | Berliner | |
| 6,346,707 B1 | 2/2002 | Vizard et al. | |
| 6,379,044 B1 | 4/2002 | Vastenaeken et al. | |
| 6,416,800 B1 | 7/2002 | Weber et al. | |
| 6,423,002 B1 | 7/2002 | Hossack | |
| 6,424,750 B1 | 7/2002 | Colbeth et al. | |
| 6,444,988 B1 | 9/2002 | Vizard | |
| 6,447,163 B1 | 9/2002 | Bani-Hashemi et al. | |
| 6,459,094 B1 | 10/2002 | Wang et al. | |
| 6,473,489 B2 | 10/2002 | Bani-Hashemi et al. | |
| 6,495,812 B1 | 12/2002 | Wurm et al. | |
| 6,531,225 B1 | 3/2003 | Homme et al. | |
| 6,615,063 B1 | 9/2003 | Ntziachristos et al. | |
| 6,686,200 B1 | 2/2004 | Dong et al. | |
| 6,762,420 B2 | 7/2004 | Homme et al. | |
| 6,948,502 B2 * | 9/2005 | Berger et al. | 128/845 |
| 7,113,217 B2 | 9/2006 | Nilson et al. | |
| 7,190,991 B2 | 3/2007 | Cable et al. | |
| 7,198,404 B2 | 4/2007 | Navab et al. | |
| 7,338,651 B2 | 3/2008 | Bornhop et al. | |
| 7,394,053 B2 | 7/2008 | Frangioni et al. | |
| 7,406,967 B2 * | 8/2008 | Callaway | 128/877 |
| 7,734,325 B2 | 6/2010 | Vizard et al. | |
| 2001/0012386 A1 | 8/2001 | Struye et al. | |
| 2003/0011701 A1 | 1/2003 | Nilson et al. | |
| 2003/0082104 A1 | 5/2003 | Mertelmeier | |
| 2003/0187344 A1 | 10/2003 | Nilson et al. | |
| 2003/0211158 A1 | 11/2003 | Frechet et al. | |
| 2004/0004193 A1 | 1/2004 | Nilson et al. | |
| 2004/0089817 A1 | 5/2004 | Long et al. | |
| 2004/0199067 A1 | 10/2004 | Bock et al. | |
| 2004/0202360 A1 | 10/2004 | Besson | |
| 2004/0249260 A1 | 12/2004 | Wang et al. | |
| 2005/0028482 A1 | 2/2005 | Cable et al. | |
| 2005/0122529 A1 | 6/2005 | Kim et al. | |
| 2005/0148846 A1 | 7/2005 | Cable et al. | |
| 2005/0175538 A1 | 8/2005 | Coquoz et al. | |
| 2005/0237423 A1 | 10/2005 | Nilson et al. | |
| 2006/0064000 A1 | 3/2006 | Vizard et al. | |
| 2006/0111613 A1 | 5/2006 | Boutillette et al. | |
| 2006/0118742 A1 | 6/2006 | Levenson et al. | |
| 2006/0173354 A1 | 8/2006 | Ntziachristos et al. | |
| 2006/0210135 A1 | 9/2006 | Kanegae | |
| 2006/0293396 A1 | 12/2006 | Bringley et al. | |
| 2007/0016077 A1 | 1/2007 | Nakaoka et al. | |
| 2007/0063154 A1 | 3/2007 | Chen et al. | |
| 2007/0087445 A1 | 4/2007 | Tearney et al. | |
| 2007/0217713 A1 | 9/2007 | Milanfar et al. | |
| 2007/0238656 A1 | 10/2007 | Harder et al. | |
| 2007/0238957 A1 | 10/2007 | Yared | |
| 2007/0281322 A1 | 12/2007 | Jaffe et al. | |
| 2008/0045797 A1 | 2/2008 | Yasushi et al. | |
| 2008/0049893 A1 | 2/2008 | Bartzke et al. | |
| 2008/0197296 A1 | 8/2008 | Uematsu | |
| 2008/0281322 A1 | 11/2008 | Sherman et al. | |
| 2009/0086908 A1 | 4/2009 | Harder et al. | |
| 2009/0116717 A1 | 5/2009 | Kohler et al. | |
| 2009/0159805 A1 | 6/2009 | Feke et al. | |
| 2009/0238434 A1 | 9/2009 | Feke et al. | |
| 2010/0022866 A1 | 1/2010 | Feke et al. | |

FOREIGN PATENT DOCUMENTS

| | | |
|---|---|---|
| EP | 1 619 548 A2 | 1/2006 |
| JP | 58-17544 U | 7/1981 |
| JP | 02-031144 | 2/1990 |
| JP | 02-052246 | 2/1990 |
| JP | 09-309845 | 12/1997 |
| JP | 11-244220 | 9/1999 |
| JP | 2001-255607 | 9/2001 |
| JP | 2001-299786 | 10/2001 |
| JP | 2003-028995 | 1/2003 |
| JP | 2004-121289 | 4/2004 |
| JP | 2005-049341 | 2/2005 |
| JP | 2005-164577 | 6/2005 |
| WO | 2004/081865 A2 | 9/2004 |
| WO | 2004/089204 A1 | 10/2004 |
| WO | 2004/108902 A2 | 12/2004 |
| WO | 2005/027730 A2 | 3/2005 |
| WO | 2007/032940 A2 | 3/2007 |

OTHER PUBLICATIONS

Virostko et al., Molecular Imaging, vol. 3, No. 4, Oct. 2004, pp. 333-342, Factors Influencing Quantification of In Vivo Bioluminescence Imaging: Application to Assessment of Pancreatic Islet Transplants.

Da Silva et al., ScienceDirect, Nuclear Instruments and Methods in Physics Research, Design of a small animal multimodality tomographer for X-ray and optical coupling: Theory and experiments, 2007, pp. 118-121.

Kruger et al., HYPR-spectral photoacoustic CT for preclinical imaging, Photons Plus Ultrasound Imaging and Sensing 2009, Proc. of SPIE, vol. 7177, 71770F-1.

User's Guide for Kodak Image Station 2000R, Aug. 2002, (172 Pages).

User's Guide for Kodak Image Station 2000MM, Nov. 2003 (168 Pages).

Yamashita et al., Mist particle diameters are related to the toxicity of waterproofing sprays: Comparison between toxic and non-toxic products, Vet Human Toxicol., (2), vol. 39, Apr. 1997, pp. 71-74.

Research Takes Many Directions, Science, vol. 303, No. 5657, Jan. 23, 2004. Advertisement (2 pages).

Sage, Linda, "The Bare Bones of Animal Imaging", The Scientist, vol. 19, Issue 4, Feb. 28, 2005. (4 pages).

"Monomolecular Multimodal Fluorescence-Radiosotope Imaging Agents", Bioconjugate Chemistry, 16(5), pp. 1232-1239, 2005.

CosmoBio report, Mar. 2004, No. 43, "Kodak Image Station 2000MM". (English translation of p. 18—5 pages).

CosmoBio report, Mar. 2004, No. 43, "Kodak Image Station 2000MM". (JP language—Foreign, 13 pages).

Kodak Image Station 2000MM Multimodal Imaging System, Internet web address: http://www.kodak.com/US/en/health/scientific/products/imgstation2000MM/index.shtml-Sep 16, 2004. (1 page).

Hussain et al., Enhanced Oral Uptake of Tomato Lectin-Conjugated Nanoparticles in the Rat, Pharmaceutical Research, vol. 14, No. 5, 1997, pp. 613-618.

V.P. Torchilin, Polymer-coated long-circulating microparticulate pharmaceuticals, J. Microencapsulation, 1998, vol. 15, No. 1, pp. 1-19.

(56) References Cited

OTHER PUBLICATIONS

Alyautdin et al., Delivery of Loperamide Across the Blood-Brain Barrier with Polysorbate 80-Coated Polybutylcyanoacrylate Nanoparticles, Pharmaceutical Research, vol. 14, No. 3, 1997, pp. 325-328.
Y. Kwon et al., Enhanced antigen presentation and immunostimulation of dendritic cells using acid-degradable cationic nanoparticles, Journal of Controlled Release 105, 2005, pp. 199-212.
Harlow et al., Antibodies—A Laboratory Manual, Chapter 5-Immunizations, 1988, pp. 91-113.
Winter et al., Man-made antibodies, Nature—vol. 349, Jan. 24, 1991, pp. 293-299.
Köhler et al., Derivation of specific antibody-producing tissue culture and tumor lines by cell fusion, Medical Research Council Laboratory of Molecular Biology, Cambridge, Eur. J. Immunol., 1976, vol. 6, pp. 511-519.
LoBuglio et al., Mouse/human chimeric conoclonal antibody in man: Kinetics and immune response, Proc. Natl. Acad. Sci., vol. 86, Jun. 1989 Immunology 4, , pp. 4220-4224.
De Verdié, et al., Reversion of multidrug resistence with polyalkycyanoacrylate nanoparticles: towards a mechanism of action, BJC British Journal of Cancer, 1997, vol. 76 (2), pp. 198-205.
Sharma et al., Novel Taxol® Formulation: Polyvinylpyrrolidone Nanoparticle-Encapsulated Taxol® for Drug Delivery in Cancer Therapy , Oncology Research, vol. 8, Nos. 7/8, pp. 281-286, 1986.
Zobel et al., Cationic Polyhexylcyanoacrylate Nanoparticles as Carriers for Antisense Oligonucleotides, Antisense & Nucleic Acid Drug Development, vol. 7, 1997, pp. 483-493.
Burke et al., Acid-Base Equilibria of Weak Polyelectrolytes in Multilayer Thin Films, Langmuir, 2003, vol. 19, No. 8, pp. 3297-3303.
Hrkach et al., Nanotechnology for biomaterials engineering; structural characterization of amphiphilic polymeric nanoparticles by $^1$H NMR spectroscopy, Biomaterials, vol. 18, No. 1, 1997, pp. 27-30.
G. Volkheimer, Übersicht, Persorption von Mikropartikeln, Pathologies, 1993, vol. 14, pp. 247-252.
Moghimi et al., Nanomedicine: current status and future prospects, The FASEB Journal, vol. 19, Mar. 2005, pp. 311-330.
Soukchareun et al., Preparation and Characterization of Antisense Oligonucleotide—Peptide Hybrids Containing Viral Fusion Peptides, Bioconjugate Chem, 1995, vol. 6, pp. 43-53.
G. Kwon et al., Block copolymer micelles as long-circulating drug vehicles, Advanced Drug Delivery Reviews, vol. 16, 1995, pp. 295-309.
Labhasetwar et al., Nanoparticle drug delivery system for restenosis, Advanced Drug Delivery Reviews, vol. 24, 1997, pp. 63-85.
Yamashita et al., Mist particle diameters are related to the toxicity of waterproofing sprays: Comparison between toxic and non-toxic products, vol. 39, 71-74, Apr. 1997.
Cleare et al., "An Experimental Study of the Mottle Produced by X-Ray Intensifying Screens," The Am. J. of Roent. and Rad. Physics, vol. 88, No. 1, pp. 168-174, Jul. 1962.
Nature Methods, "Harnessing multimodality to enhance quantification and reproducibility of in vivo molecular imaging data", by Gilbert D. Feke et al., Nov. 2008, 2 pages.
Biochem Biophys Res Commun, Inspiration for Life Science, "Anti Human Galectin 3 Polyelonal Antibody", by W. Zhu, 280:11831188, 2001, 2 pages.
IEEE Transactions on Nuclear Science, "Iodine 125 Imaging in Mice Using NaI(TI)/Flat Panel PMT Integral Assembly", by M.N. Cinti et al., vol. 54, No. 3, Jun. 2007, pp. 461-468.
Mat. Res. Soc. Symp. Proc., "Optimising of the Physico-Chemical Properties of a Novel Barium Sulphate Preparation for the X-Ray Examination of the Intestine", by Barbara Laermann et al., vol. 550, 1999 Materials Research Society, pp. 59-64.
Am. Assoc. Phys. Med., "MicroCT scanner performance and considerations for vascular specimen imaging", by Michael Marxen et al., Med. Phys. 31 (2), Feb. 2004, pp. 305-313.
Rat Atlas Project, Internet Study: Hubei Bioinformatics and Molecular Imaging Key Laboratory, The Key Laboratory of Biomedical Photonics of Ministry of Education, College of Life Science and Technology, Huazhong University of Science and Technology, http://www.vch.org.cn/mice/method.aspx , printed from Internet on Sep. 12, 2011, (4 pages).
Kodak Image Station 2000MM Multi-Modal Imager, Kodak Scientific Imaging Systems—advertisment—Fall/2003 (2 pages).
Proceedings of the American Thoracic Society, "Micro-Computed Tomography of the Lungs and Pulmonary-Vascular System", by Erik L. Ritman, 2 pp. 477-480, 2005.
The Journal of Nuclear Medicine, "Significance of Incidental 18F-FDG Accumulations in the Gastrointestical Tract in PET/CT: Correlation with Endoscopic and Histopathologic Results", by Ehab M. Kamel et al., vol. 45, No. 11, pp. 1804-1810, 2004.
Corresponding WO = PCT/us2005/032504, International Preliminary Report on Patentability, dated Mar. 27, 2007, 8 pages.
Corresponding CN = CN 200580031808.5—SIPO First Office Action dated Dec. 4, 2009. 14 pages.
International Search Report, International Application No. PCT/US2005/032504, dated Dec. 23, 2005, 10 pages.
International Search Report, International Application No. PCT/US2008/010304, dated Dec. 8, 2008, 5 pages.
International Search Report, International Application No. PCT/US2009/000457, dated Aug. 21, 2009, 3 pages.
Hamamatsu Photonics K.K., Catalog No. SFAS0017E06, X-Ray Line Scan Camera, Jun. 2010, 4 pages.
Hamamatsu Photonics K.K., Publication No. TMCP1031E04, X-Ray Scinitllator, Jun. 2009, 4 pages.
European Search Report dated Apr. 8, 2011 for European Application No. 10 01 2074.0, 2 pages.

* cited by examiner

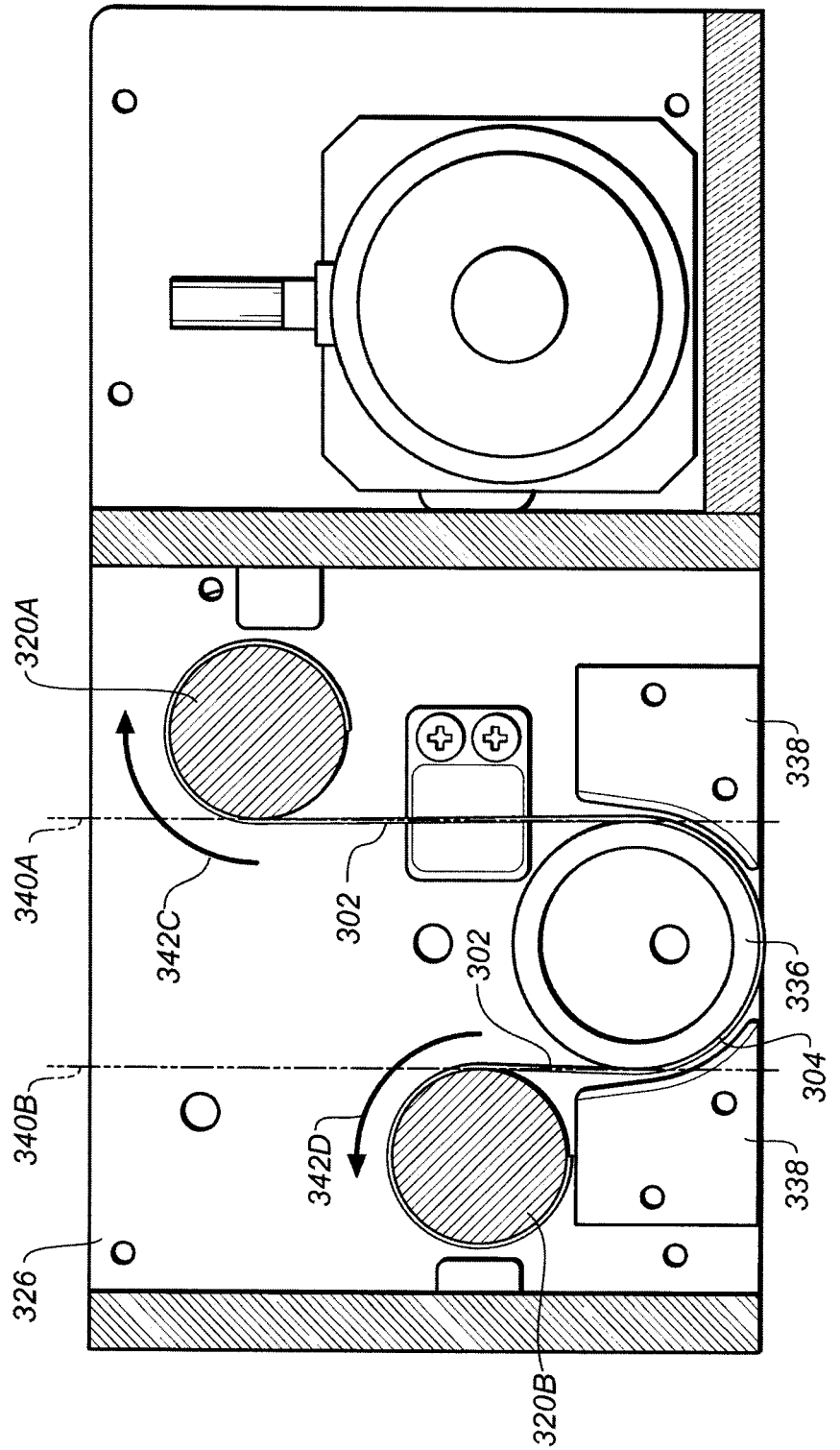

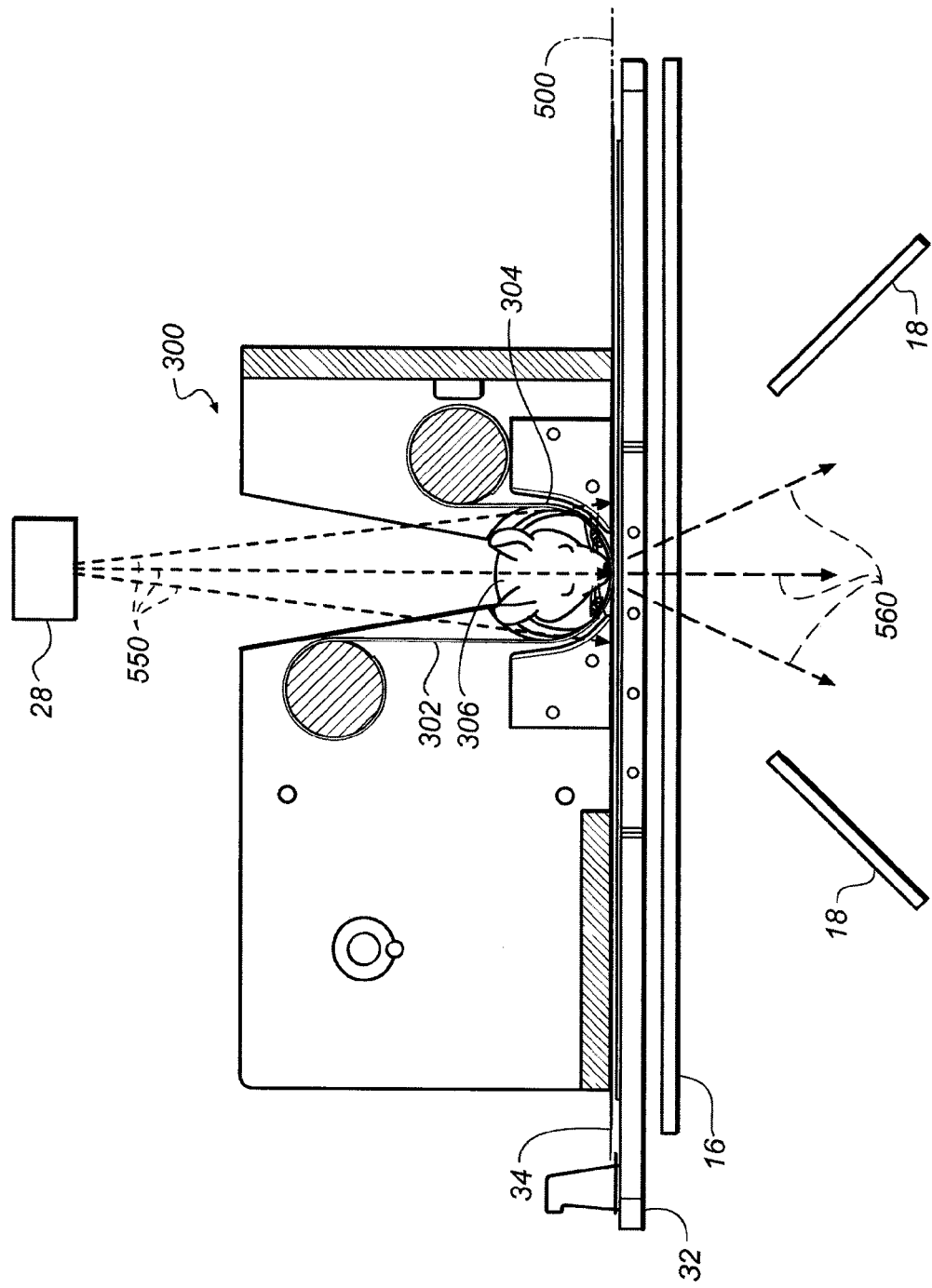

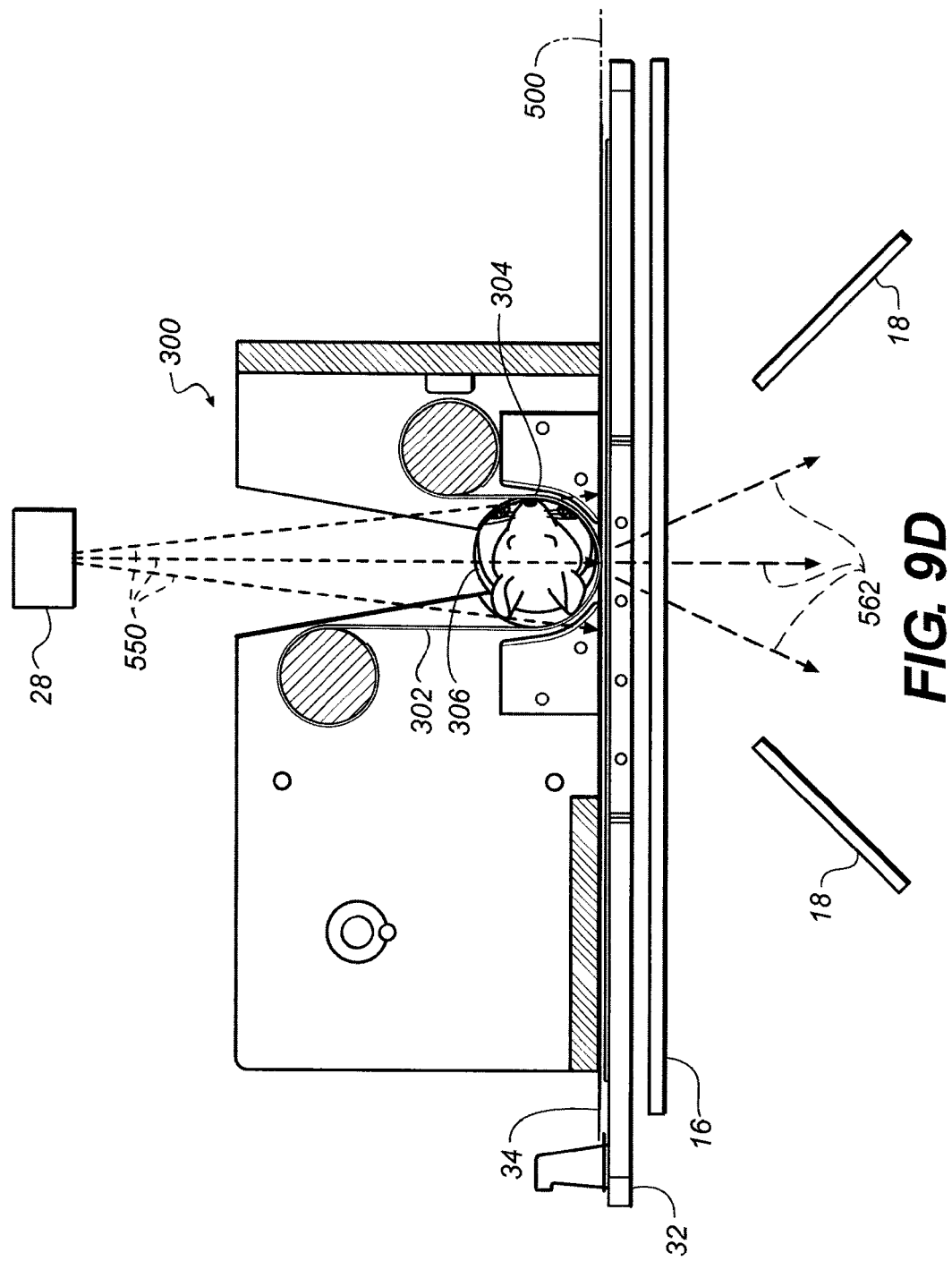

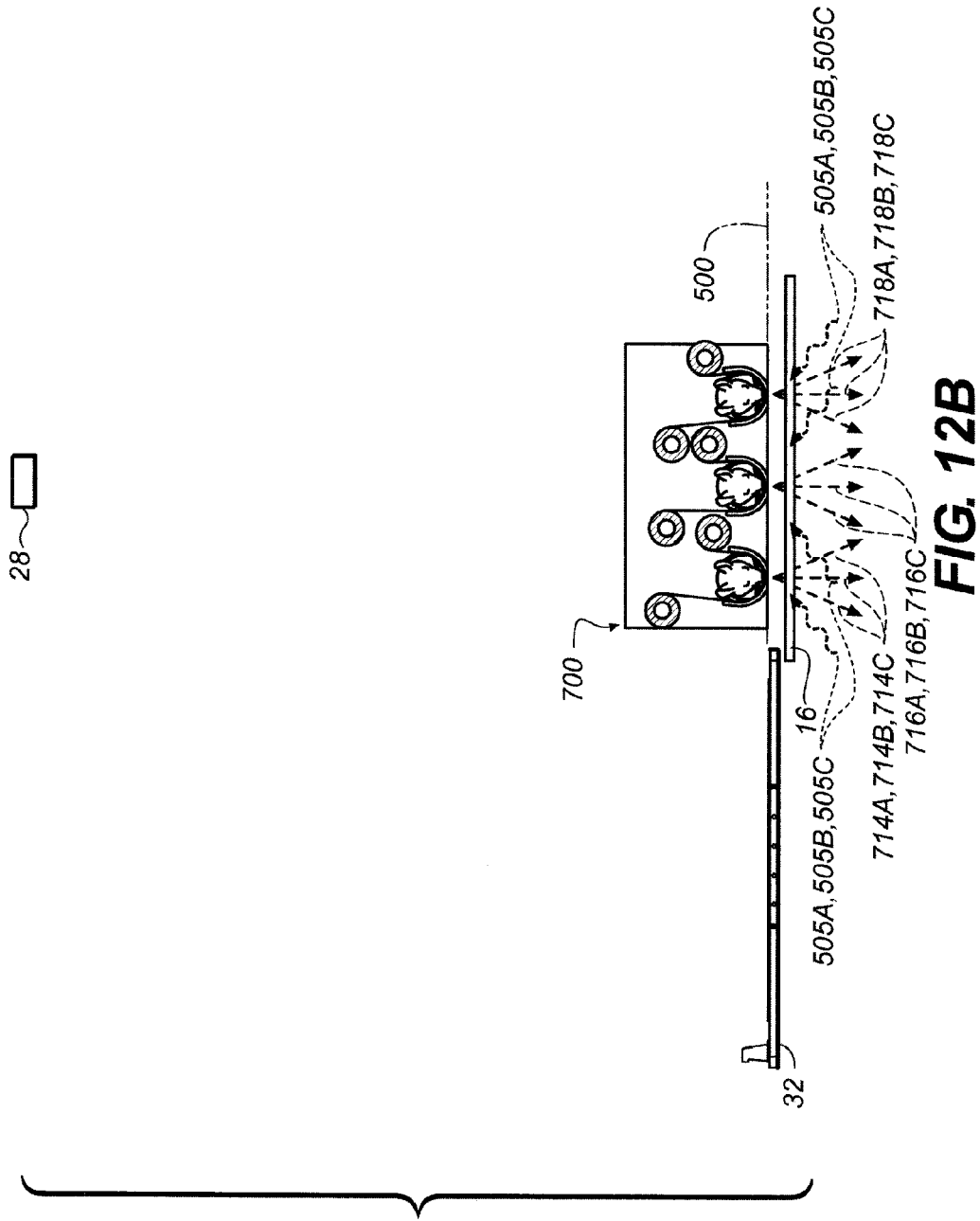

US 8,660,631 B2

TORSIONAL SUPPORT APPARATUS AND METHOD FOR CRANIOCAUDAL ROTATION OF ANIMALS

CROSS REFERENCE TO RELATED APPLICATIONS

Reference is made to and priority is claimed from provisional U.S. Patent Application Ser. No. 61/131,948, filed Jun. 13, 2008 by Feke et al entitled TORSIONAL SUPPORT APPARATUS FOR CRANIOCAUDAL ROTATION OF ANIMALS, the disclosure of which is incorporated by reference into this specification.

This application is a Continuation-In-Part of the following commonly assigned, copending U.S. Patent Applications, the disclosure of each of which also is incorporated by reference into this specification:

U.S. Ser. No. 11/221,530 filed Sep. 9, 2005 by Vizard et al., entitled APPARATUS AND METHOD FOR MULTI-MODAL IMAGING;

U.S. Ser. No. 12/196,300 filed Aug. 22, 2008 by Harder et al., entitled APPARATUS AND METHOD FOR MULTI-MODAL IMAGING USING NANOPARTICLE MULTI-MODAL IMAGING PROBES;

U.S. Ser. No. 12/354,830 filed Jan. 16, 2009 by Feke et al., entitled APPARATUS AND METHOD FOR MULTI-MODAL IMAGING;

U.S. Ser. No. 12/381,599 filed Mar. 13, 2009 by Feke et al., entitled METHOD FOR REPRODUCING THE SPATIAL ORIENTATION OF AN IMMOBILIZED SUBJECT IN A MULTI-MODAL IMAGING SYSTEM; and U.S. Ser. No. 12/411,432 filed Mar. 26, 2009 by Feke, entitled APPARATUS AND METHOD FOR FLUORESCENCE IMAGING AND TOMOGRAPHY USING SPATIALLY STRUCTURED ILLUMINATION.

FIELD OF THE INVENTION

The invention relates generally to the field of imaging systems, and more particularly to the imaging of objects. More specifically, the invention relates to a torsional support apparatus for craniocaudal rotation of animals to enable multiple-view imaging.

BACKGROUND OF THE INVENTION

Electronic imaging systems are known for enabling imaging of animals, for example mice. An exemplary electronic imaging system 10 is shown in FIGS. 1A, 1B, 1C, and 1D. An example of this system is the KODAK In-Vivo Imaging System FX Pro. System 10 includes a light source 12; a sample environment 14 which allows access to the object or objects being imaged; an optically transparent platen 16 disposed within sample environment 14; an epi-illumination delivery system comprised of fiber optics 18 which are coupled to light source 12 and direct conditioned light (of appropriate wavelength and divergence) toward platen 16 to provide bright-field or fluorescence imaging; an optical compartment 20 which includes a mirror 22 and a lens and camera system 24; a communication and computer control system 26 which can include a display device, for example, a computer monitor; a microfocus X-ray source 28; an optically transparent planar animal support member 30 on which objects may be immobilized and stabilized by gravity; and a high-resolution phosphor screen 32, adapted to transduce ionizing radiation to visible light by means of high-resolution phosphor sheet 34, which is proximate to animal support member 30 and removable along direction indicated by arrow 36, by conventional means such as a motor and lead screw arrangement, not illustrated. In the illustrated imaging system, lens and camera system 24 are located below support member 30; however, those skilled in the art understand that the system could be reconfigured to provide for imaging from above the support member or from any suitable angle.

Light source 12 can include an excitation filter selector for fluorescence excitation or bright-field color imaging. Sample environment 14 is preferably light-tight and fitted with light-locked gas ports for environmental control. Such environmental control might be desirable for controlled X-ray imaging or for life-support of particular biological specimens. Imaging system 10 can include an access means or member 38 to provide convenient, safe and light-tight access to sample environment 14. Access means are well known to those skilled in the art and can include a door, opening, labyrinth, and the like. Additionally, sample environment 14 is preferably adapted to provide atmospheric control for sample maintenance or soft X-ray transmission (e.g., temperature/humidity/alternative gases and the like). Camera and lens system 24 can include an emission filter wheel for fluorescent imaging. Examples of electronic imaging systems capable of multimodal imaging are described in the previously mentioned, copending, commonly assigned applications of Vizard et al, Feke and Feke et al.

In operation, the system is configured for a desired imaging mode chosen among the available modes including X-ray mode, radioactive isotope mode, and optical imaging modes such as bright-field mode, fluorescence mode, luminescence mode, and an image of an immobilized subject, such as a mouse 40 under anesthesia and recumbent upon optically transparent animal support member 30, is captured using lens and camera system 24. System 24 converts the light image into an electronic image, which can be digitized. The digitized image can be displayed on the display device, stored in memory, transmitted to a remote location, processed to enhance the image, and/or used to print a permanent copy of the image. The system may be successively configured for capture of multiple images, each image chosen among the available modes, whereby a synthesized image, such as a composite overlay, is generated by the combination of the multiple captured images.

Mouse 40 may successively undergo craniocaudal rotation and immobilization directly onto planar animal support member 30 in various recumbent body postures, such as prone, supine, laterally recumbent, and obliquely recumbent, whereby the mouse is stabilized by gravity for each body posture, to obtain multiple views, for example ventral and lateral views as described in "Picture Perfect: Imaging Gives Biomarkers New Look", P. Mitchell, *Pharma DD*, Vol. 1, No. 3, pp. 1-5 (2006). As seen in FIG. 1D, a plurality of animals 40 may be imaged at the same time, only one being shown for ease of illustration. Animals may be rotated manually about their craniocaudal axes to provide different viewing angles, as indicated by arrow 42.

Direct immobilization of the animal in a recumbent posture onto an optically transparent planar support and imaging from below is advantageous for several reasons. First, the range of craniocaudal rotation angles, and hence the range of view angles, is unlimited and continuous. Second, the human experimenter has access to the animal. For example, where an experiment requires an intimate delivery, such as by injection, oral gavage, inhalation, transrectal delivery, transdermal delivery, or transmucosal delivery, of a substance, such as a drug, optical fluorescence imaging agent, X-ray contrast agent, or radionuclide imaging agent, to an animal, it is often desirable to capture images of the animal both prior to and after delivery of the substance without substantially physically disturbing the animal in the imaging system. This is especially desirable when studying the perfusion and clearance of imaging or contrast agents or therapeutic response of a drug over time. Third, the human experimenter has access to the immediate environment around the animal. For example, it is often desirable to clean the immediate environment of residue, including animal urine, feces, or surface debris that might otherwise cause imaging artifacts. Fourth, by virtue of stabilization by gravity, minimal manipulation and restraint of the animal is required to place it in the imaging system in a desired posture, hence facilitating an ergonomic protocol for the human experimenter. Fifth, recumbent postures are desired to minimize physiological stress on the animal. Sixth, the optically transparent support provides a physical surface to serve as a reference for a focal plane for the lens and camera system to facilitate the capture of sharp, well-resolved images. Seventh, the optically transparent support facilitates multimodality imaging in that a removable phosphor screen can be located proximally to the support surface, therefore providing a common focal plane for both the optical imaging modes (bright-field mode, fluorescence mode, and luminescence mode) and the imaging modes requiring a phosphor screen (X-ray mode and radioactive isotope mode); the common focal plane is necessary for precise co-registration of overlaid images from the optical imaging modes and the imaging modes requiring a phosphor screen. Eighth, the imaging light path is stationary and common for all view angles and all imaging modes, thereby providing for simple, inexpensive components to define the imaging light path.

On the other hand, direct immobilization of a recumbent animal onto a planar support is disadvantageous in that in known imaging systems a means is lacking to precisely control the craniocaudal rotation angle, and hence the view angle, of the animal, for example to ±5 degree precision. Improved control of the view angle would improve the experimenter's ability to quantify molecular signals. In the case of optical molecular signals obtained from fluorescence and luminescence modes, the signal is dependent upon the depth of tissue between the animal surface and the distributed fluorescent or luminescent content inside the animal through which the light must travel. That depth of tissue is dependent upon the animal's posture. In the case of radioactive isotope molecular signals, the signal is dependent upon the distance of the distributed radioactive isotope inside the animal from the phosphor screen. That distance is dependent upon the animal's posture.

Improved control of the view angle also would improve the experimenter's ability to reproduce the spatial orientation of an animal. For example, an animal used in a longitudinal imaging study is loaded into an imaging system and immobilized for a first time, imaged for the first time, unloaded from the imaging system, loaded into the imaging system and immobilized for an at least second time, and imaged for the at least second time, thereby producing a first-time set of images and an at least second-time set of images. If the spatial orientation of the animal, for example the craniocaudal rotation angle of the animal, with respect to the imaging system is different between the first time and the at least second time, then the at least second-time set of images may be affected by the difference in the spatial orientation compared to the first-time set of images. This difference may result in artifacts, such as relative attenuation or enhancement of a molecular signal, upon comparison to the first-time set of multimodal molecular images. Similarly, this difference may lead to a result that the first-time set of images and the at least second-time set of images will not be co-registered, thereby degrading the quantitation provided by a simple regions-of-interest analysis wherein a single regions-of-interest template is applied to both the first-time set of images and the at least second-time set of images.

For example, when a plurality of animals are used in an imaging study, and are loaded into an imaging system and immobilized, whereby the loading and immobilization may be performed serially at a given spatial location within the field of view of the imaging system, or may be performed in parallel across a plurality of spatial locations in the field of view of the imaging system, the spatial orientations of the animals, for example the craniocaudal rotation angles, may differ among the plurality of animals, so that each set of images for each animal may be affected by the difference in the spatial orientation, thereby resulting in artifacts, such as relative attenuation or enhancement of a molecular signal, in one set of images compared to another set of images.

If animals are loaded serially at a given spatial location within the field of view, then the sets of images may not be co-registered among the plurality of animals due to differences in the spatial orientations of the animals, for example the craniocaudal rotation angles, thereby degrading quantitation provided by a simple regions-of-interest analysis wherein a single regions-of-interest template is applied to the sets of images corresponding to the plurality of animals.

If animals are loaded in parallel across a plurality of spatial locations in the field of view of the imaging system, then regions of interest defined for one animal may not be spatially translatable to the other animals by the simple difference between the spatial locations of the animals due to differences in the spatial orientations, for example the craniocaudal rotation angles, of the animals at their locations, thereby degrading quantitation provided by a simple regions-of-interest analysis wherein an array-like regions-of-interest template (i.e., multiple copies of a set of regions of interest across the field of view) is applied to the set of images.

Although imaging systems are known that can obtain multiple views of an animal with a stationary camera system wherein the view angle is more precisely controlled, none of these provides all of the advantages of direct immobilization of a recumbent animal onto a support. Strapping the subject down onto an angularly adjustable goniometer stage and imaging from above is described in "Factors Influencing Quantification of In Vivo Bioluminescence Imaging: Application to Assessment of Pancreatic Islet Transplants", J. Virostko et al., *Molecular Imaging*, Vol. 3, No. 4, pp. 333-342 (2004). Suspending the animal in a holder which is clamped onto a rotation stage is described in "Systems and Methods for Bioluminescent Computed Tomographic Reconstruction", Wang et al., U.S. patent application Ser. No. 10/791,140, Publication US2004/0249260. Placing the subject into a rotatable tube is described in "System and Method for Visualizing Three-dimensional Tumor Locations and Shape from Two-dimensional Bioluminescence Images", D. Metaxas et al., U.S. Provisional Patent Application Ser. No. 60/715,610, Publication WO/2007/032940; and in "Design of a Small Animal Multimodality Tomographer for X-Ray and Optical Coupling: Theory and experiments", da Silva et al., Nuclear Instruments and Methods in Physics Research A, Vol. 571, Nos. 1-2, pp. 118-121, (2007). Employing a rotating mirror and a translating subject stage is described in "Multi-view imaging apparatus", D. Nilson et al., U.S. Pat. No. 7,113,217. Employing a multiple mirror assembly that surrounds a portion of the subject to direct additional views to the camera system is described in "Systems and methods for in-vivo optical imaging and measurement", R. Levenson and C. Hoyt, U.S. patent application Ser. No. 11/295,701, Publication US2006/0118742.

While systems of the types described in the just-mentioned publications and patents may have achieved certain advantages, each of them also exhibits one or more of the following disadvantages. The adjustable stage has a limited angular range thereby limiting the range of view angles. The animal holder obstructs the view for certain view angles. The human experimenter has limited access to the immediate environment around the animal. Significant manipulation of the animal is required to strap it down to prevent sliding on the adjustable stage, to suspend it in the holder or to load it into a tube in a desired posture. A physical surface to serve as a reference for a focal plane is not provided. A surface for the proximal location of a phosphor screen is not provided. The animal is not recumbent, hence it is subject to significant physiological stress. The imaging light path is different for every view angle, thereby requiring complex, expensive components to define the imaging light path. A multiple mirror assembly has a limited, discontinuous angular range, thereby limiting the range of view angles.

Imaging systems also are known that can obtain multiple views of an animal, comprised of one or more lens and camera systems mounted on a gantry that may be rotatable about the animal. For example, see "Method and system for free space optical tomography of diffuse media", V. Ntziachristos and J. Ripoll, U.S. patent application Ser. No. 10/543,728 and U.S. Patent Application Publication 2006/0173354; and "Combined X-ray and Optical Tomographic Imaging System", W. Yared, U.S. patent application Ser. No. 11/643,758 and U.S. Patent Application Publication 2007/0238957. However, such systems are significantly more complex and expensive compared to a single, stationary imaging light path common for all view angles and all imaging modes.

In addition, photoacoustic tomography systems are known for enabling photoacoustic tomography of animals, for example mice. An exemplary photoacoustic tomography system is described in "HYPR-spectral photoacoustic CT for preclinical imaging", Kruger et al., Proc. SPIE, Vol. 7177, 71770F (2009). The system is comprised of an array of ultrasound sensors disposed in a bowl. The bowl has an optically transparent window in the bottom. In operation, the bowl is filled with an optically transparent acoustic coupling medium, such as a liquid or gel, an optically transparent membrane is placed at the top surface of the acoustic coupling medium, the animal is immobilized and placed on the membrane in a recumbent posture, pulsed light is provided through the window to the animal, the light is absorbed by endogenous and/or exogenous material in the animal, the material releases energy as ultrasound, the ultrasound is detected by the array of sensors, and a electronic system performs a tomographic reconstruction based on the detected ultrasound. Because the penetration depth of the light is limited by absorption and scatter in the animal, it is desirable to be able to position the animal in a variety of postures to access the various anatomical features of the animal. In known photoacoustic tomography systems, animals may be rotated manually about their craniocaudal axes to provide different viewing angles. However, direct immobilization of a recumbent animal onto a membrane is disadvantageous in that in known photoacoustic tomography systems a means is lacking to precisely control the craniocaudal rotation angle, and hence the view angle, of the animal, for example to ±5 degree precision. Improved control of the view angle would improve the experimenter's ability to quantify photoacoustic data. For example, photoacoustic calibrations that depend on the tissue depth, and hence the animal posture, could be more precisely determined. Also, different photoacoustic tomographic sections from a series of different view angles could be precisely stitched together given precise knowledge of the view angle.

SUMMARY OF THE INVENTION

The present invention not only provides all of the advantages previously described for directly immobilizing the animal in a recumbent posture on an optically transparent planar support and imaging the immobilized animal from above, below or from any suitable angle; but also provides unique features for adjusting the craniocaudal rotation angle and the view angle.

An apparatus in accordance with the invention is useful for imaging an animal having a craniocaudal axis. The apparatus may include an elongated member for supporting such an animal in a position with its craniocaudal axis transverse to an axis of elongation of the elongated member; means for forming the elongated member into an upwardly open, U-shaped loop, the loop being sized for receiving and engaging such an animal; means for moving the support member in a direction of the axis of elongation while maintaining the U-shaped loop, whereby movement of the support member applies torsion to such an animal so that it is rotated about its craniocaudal axis; and means for imaging such an animal at various angles of craniocaudal rotation. Imaging may be done from above, below or from any suitable angle.

A method in accordance with the invention is useful for imaging an animal having a craniocaudal axis. The method may include steps of providing an elongated member having an axis of elongation and longitudinally extending edges; forming the elongated member into an upwardly open, U-shaped loop, the loop being sized for receiving and engaging the animal; supporting the animal in the U-shaped loop with the craniocaudal axis transverse to the axis of elongation; moving the support member sequentially in a direction of the axis of elongation while maintaining the U-shaped loop, whereby torsion is applied to the animal so that it is rotated to various angles about the craniocaudal axis; and imaging the animal at various angles of craniocaudal rotation. Imaging may be done from above, below or from any suitable angle.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 3G shows a diagrammatic front, sectional view of the torsional support apparatus of FIG. 2A during installation of the support film.

FIG. 7B shows a diagrammatic rear view of the torsional support apparatus and removable high-resolution phosphor screen of FIG. 2A where the animal has undergone craniocaudal rotation to a prone posture, the high-resolution phosphor screen has been installed, and the animal is being imaged using an X-ray imaging mode.

FIG. 9D shows a diagrammatic rear view of the torsional support apparatus and removable high-resolution phosphor screen of FIG. 2A where the animal has underwent craniocaudal rotation to a laterally recumbent posture, the high-resolution phosphor screen has been installed, and the animal is being imaged using an X-ray imaging mode.

FIG. 12B shows a diagrammatic rear view of the multiple torsional support apparatus of FIG. 12A and removable high-resolution phosphor screen where the phosphor screen has been removed and the animals are being imaged using an optical imaging mode.

DETAILED DESCRIPTION OF THE INVENTION

Figure 1A:
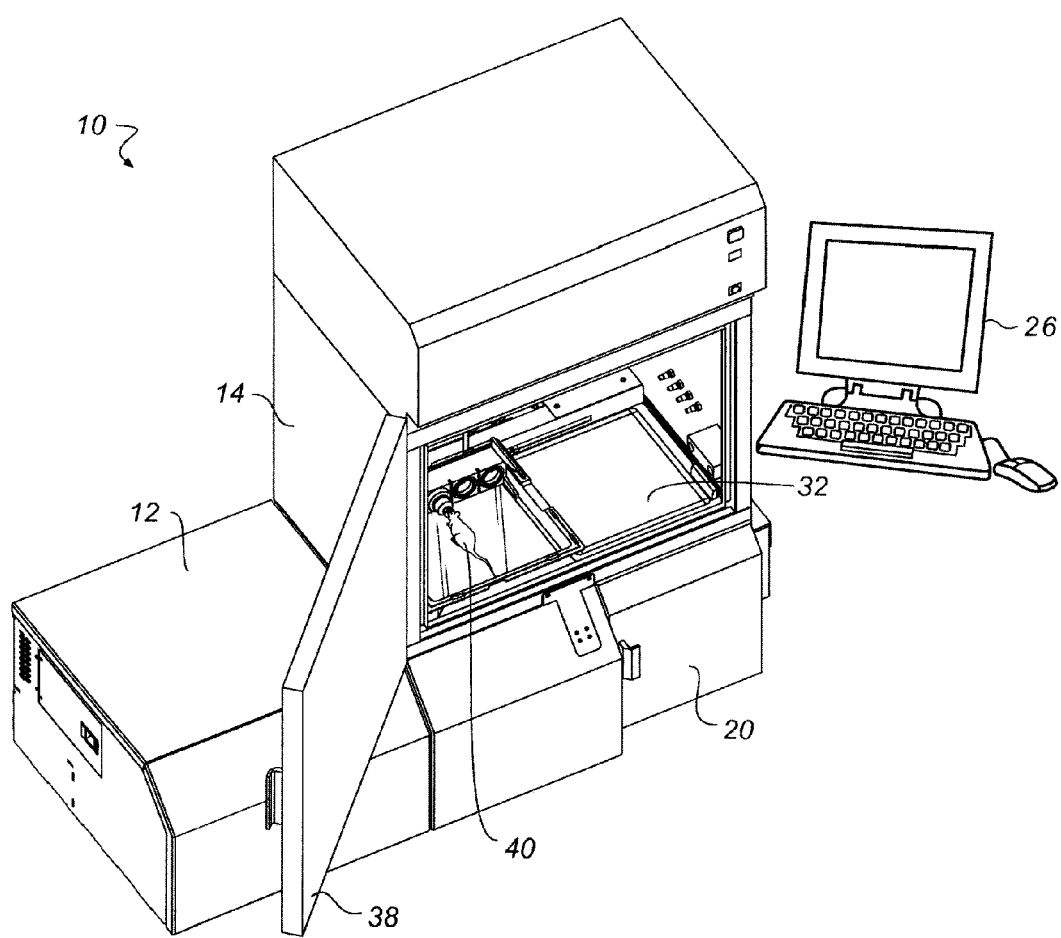
FIG. 1A shows a perspective view of a known electronic imaging system including a removable high-resolution phosphor screen.
Figure 1C:
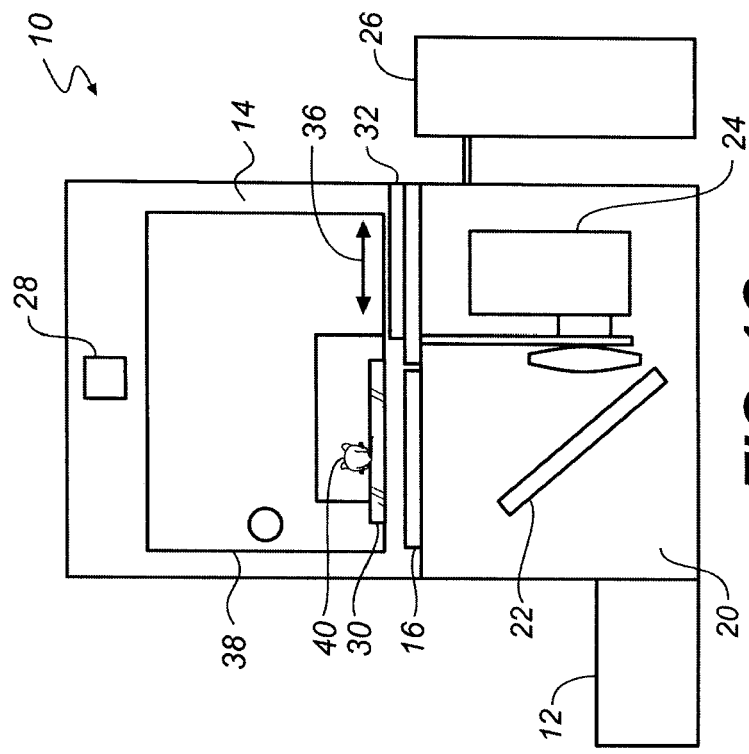
FIG. 1C shows a diagrammatic front view of the imaging system of FIG. 1A.
Figure 1B:
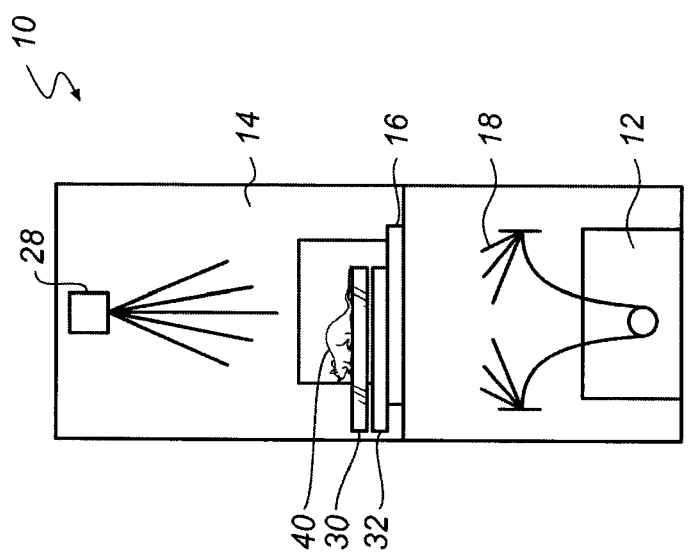
FIG. 1B shows a diagrammatic side view of the imaging system of FIG. 1A.
Figure 1D:
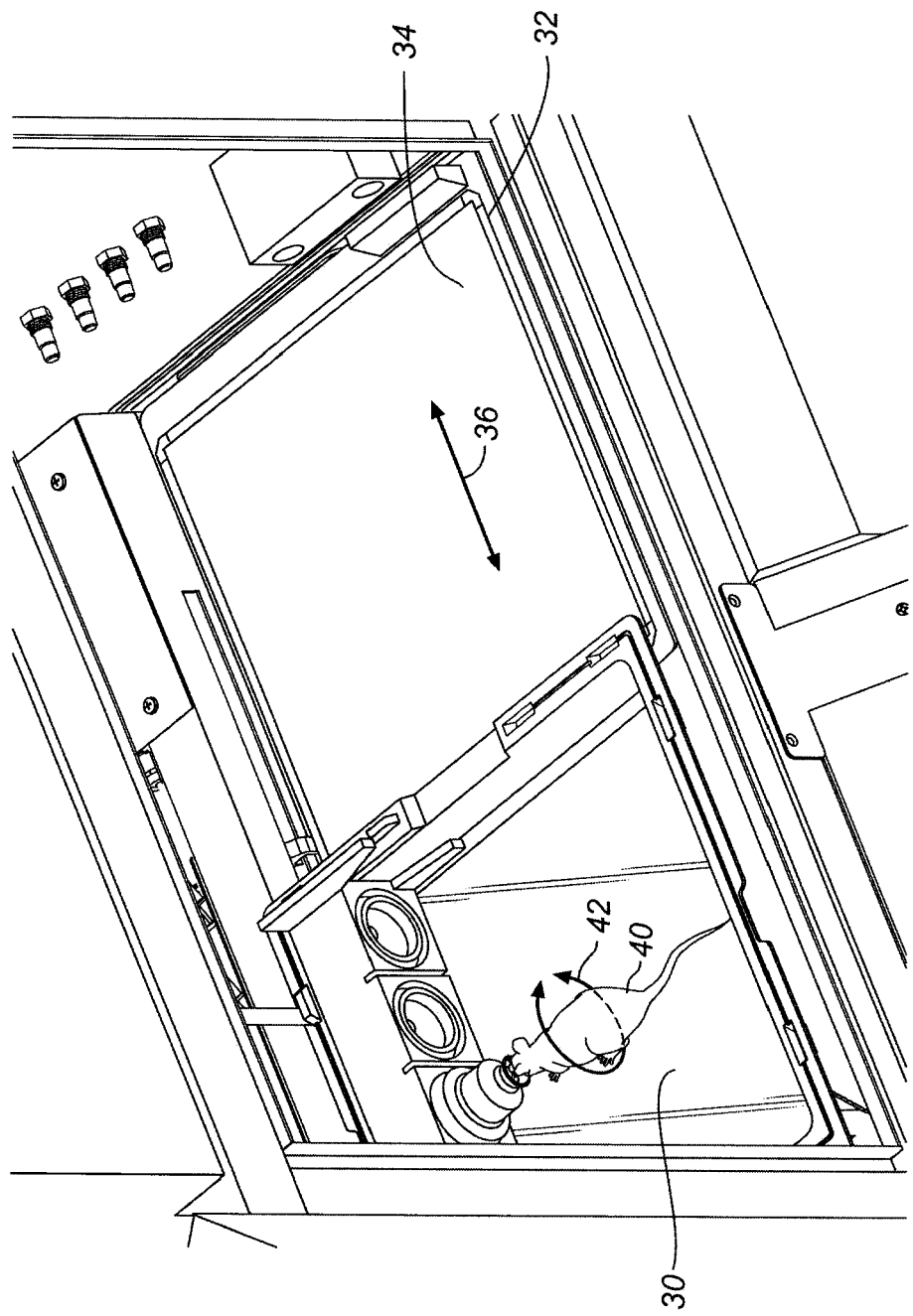
FIG. 1D shows a detailed perspective view of the imaging system of FIG. 1A.

The invention now will be described in detail with particular reference to certain preferred embodiments thereof, but it will be understood that variations and modifications can be effected within the spirit and scope of the invention. The following is a detailed description of the preferred embodiments of the invention, reference being made to the drawings in which the same reference numerals identify the same elements of structure in each of the several figures.

Figure 2A:
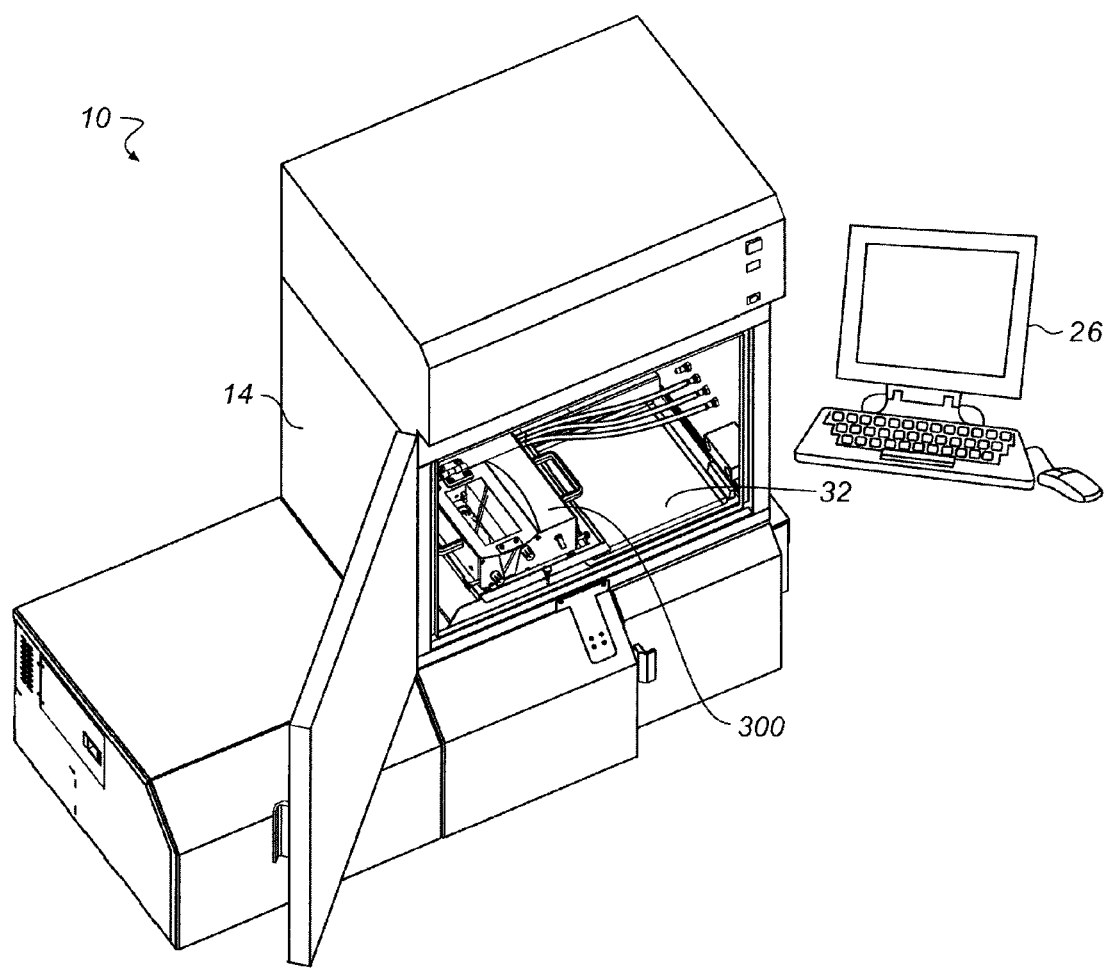
FIG. 2A shows a perspective view of an electronic imaging system with a movable high-resolution phosphor screen and a torsional support apparatus for the animal in accordance with the present invention.
Figure 2B:
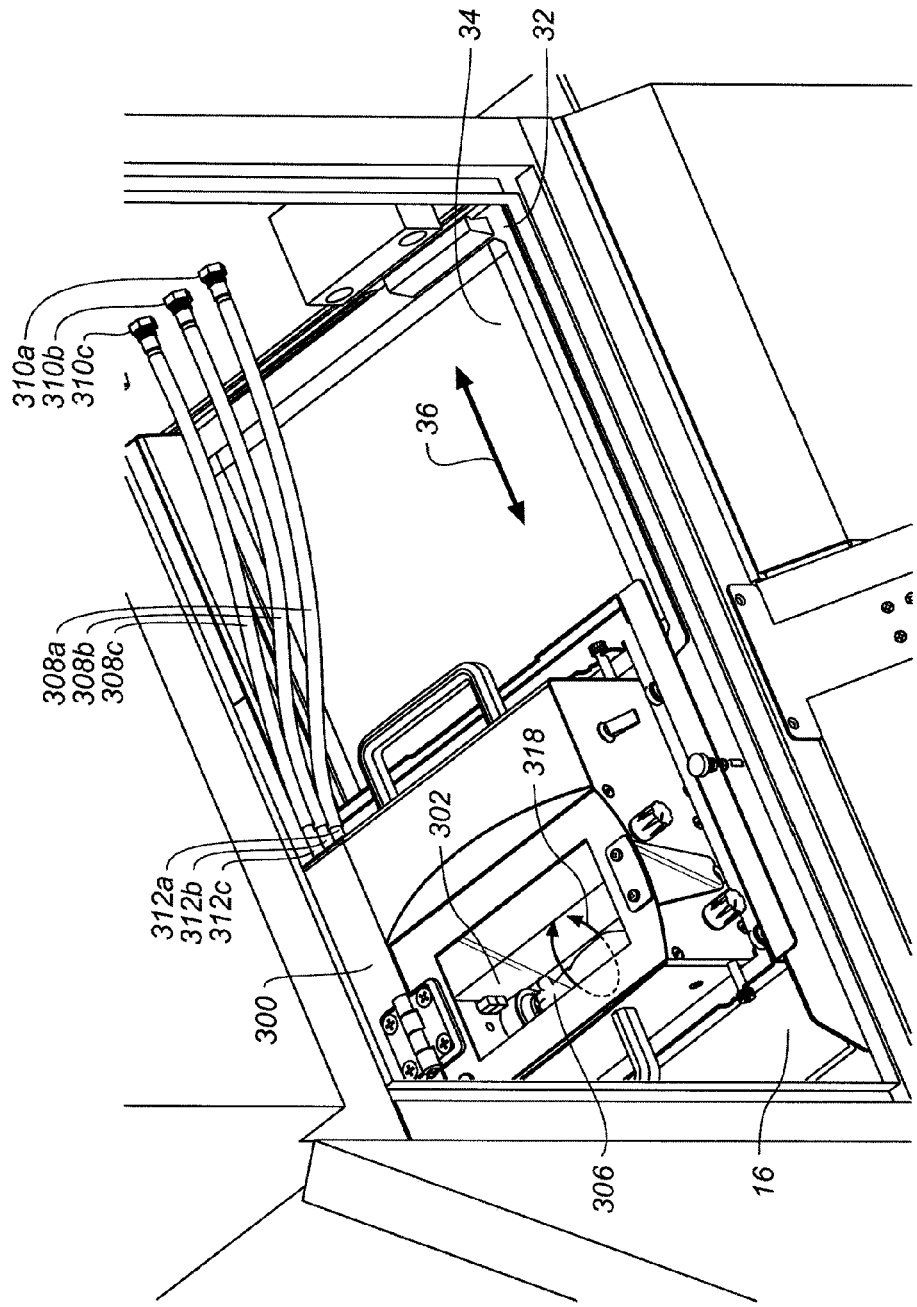
FIG. 2B shows an enlarged, fragmentary perspective view of the imaging system of FIG. 2A.
Figure 5A:
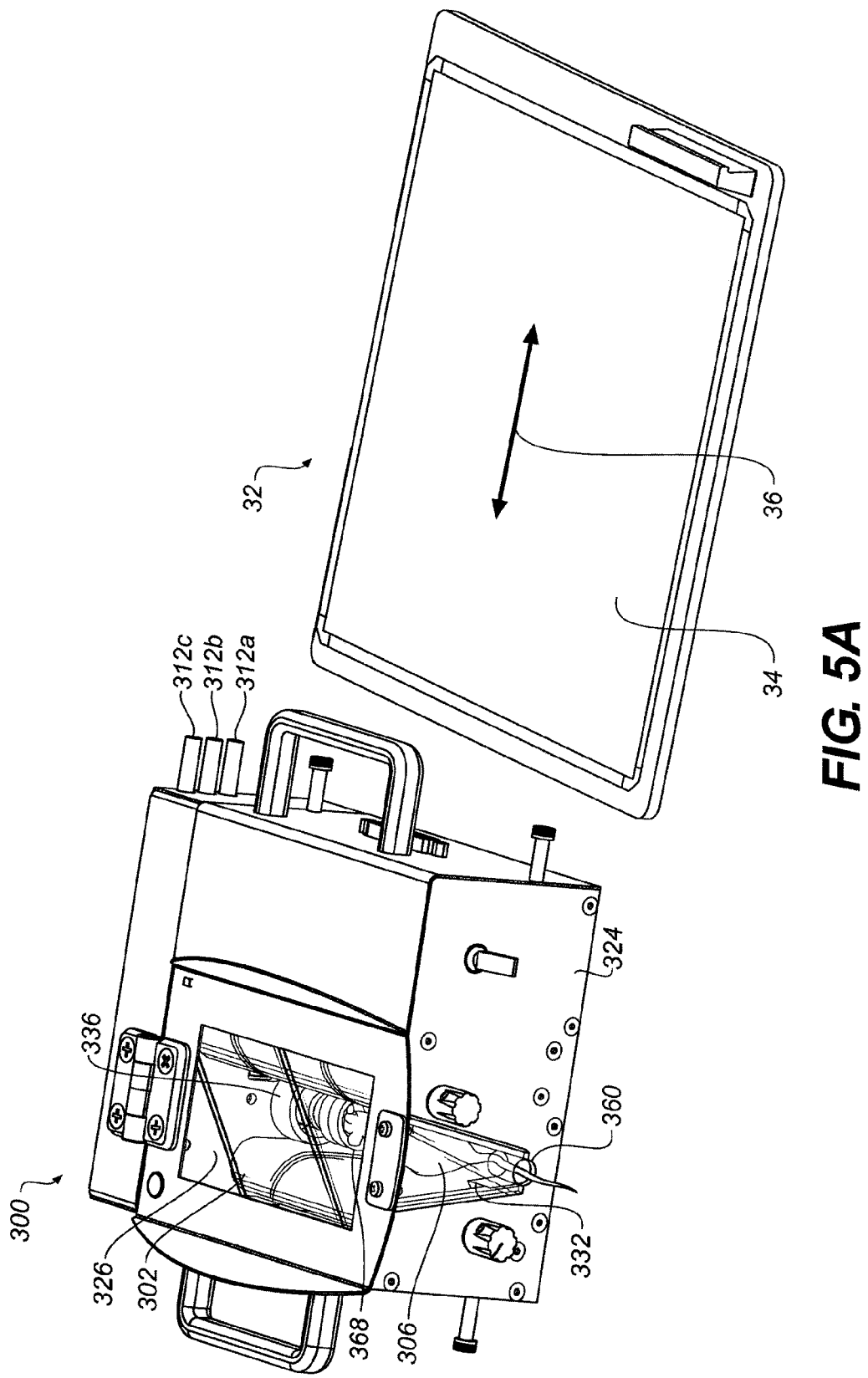
FIG. 5A shows a perspective view of the torsional support apparatus and removable high-resolution phosphor screen of FIG. 2A where the animal is recumbent in a prone posture.
Figure 5B:
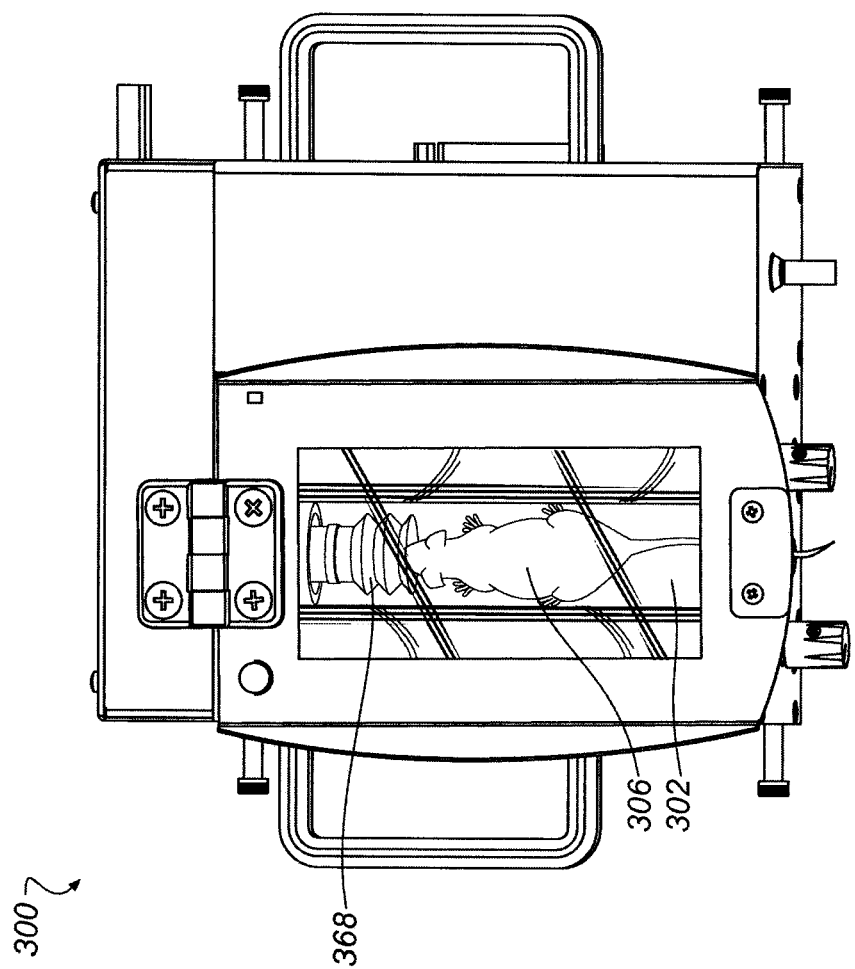
FIG. 5B shows a view from above the torsional support apparatus of FIG. 2A where the animal is recumbent in a prone posture.
Figure 5C:
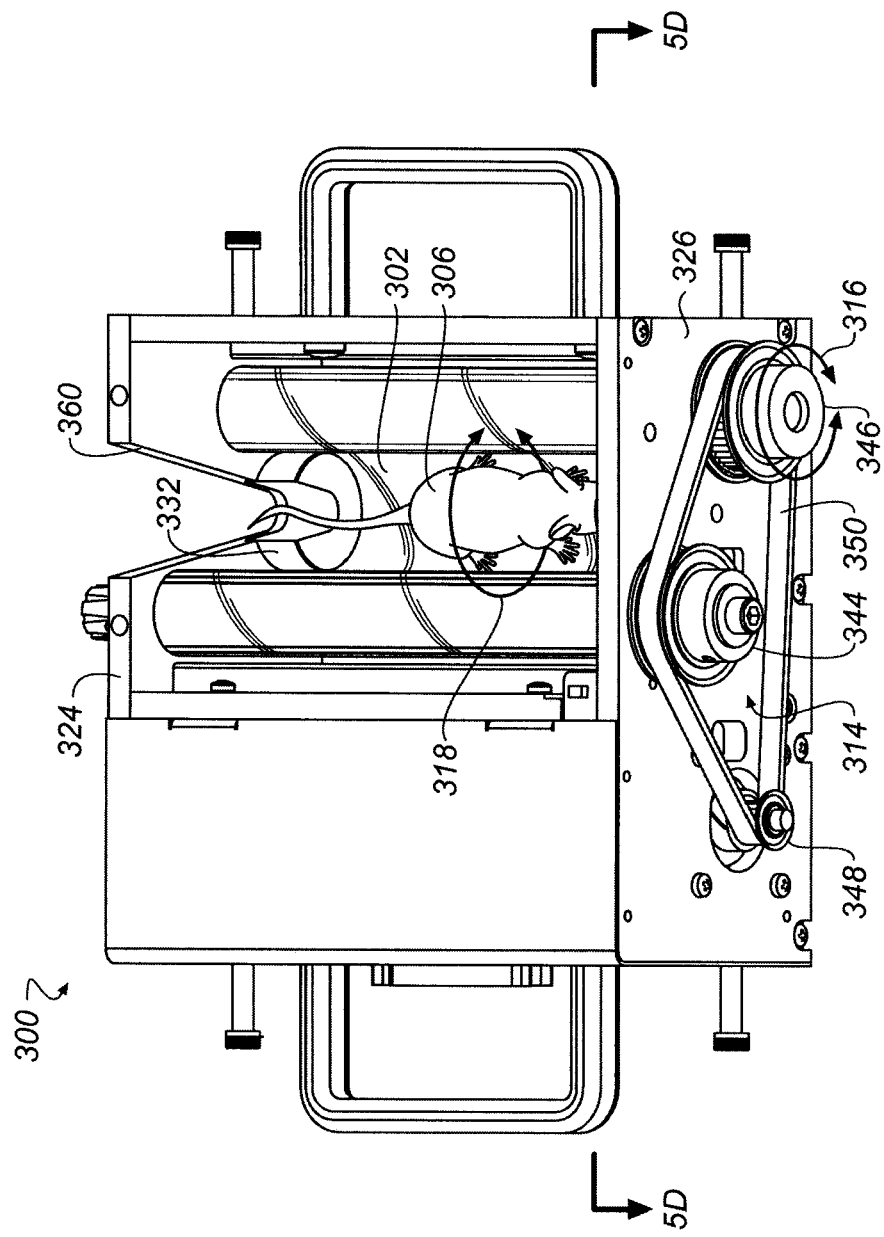
FIG. 5C shows a perspective, fragmentary view from the rear of the torsional support apparatus of FIG. 2A where the animal is recumbent in a prone posture.
Figure 5D:
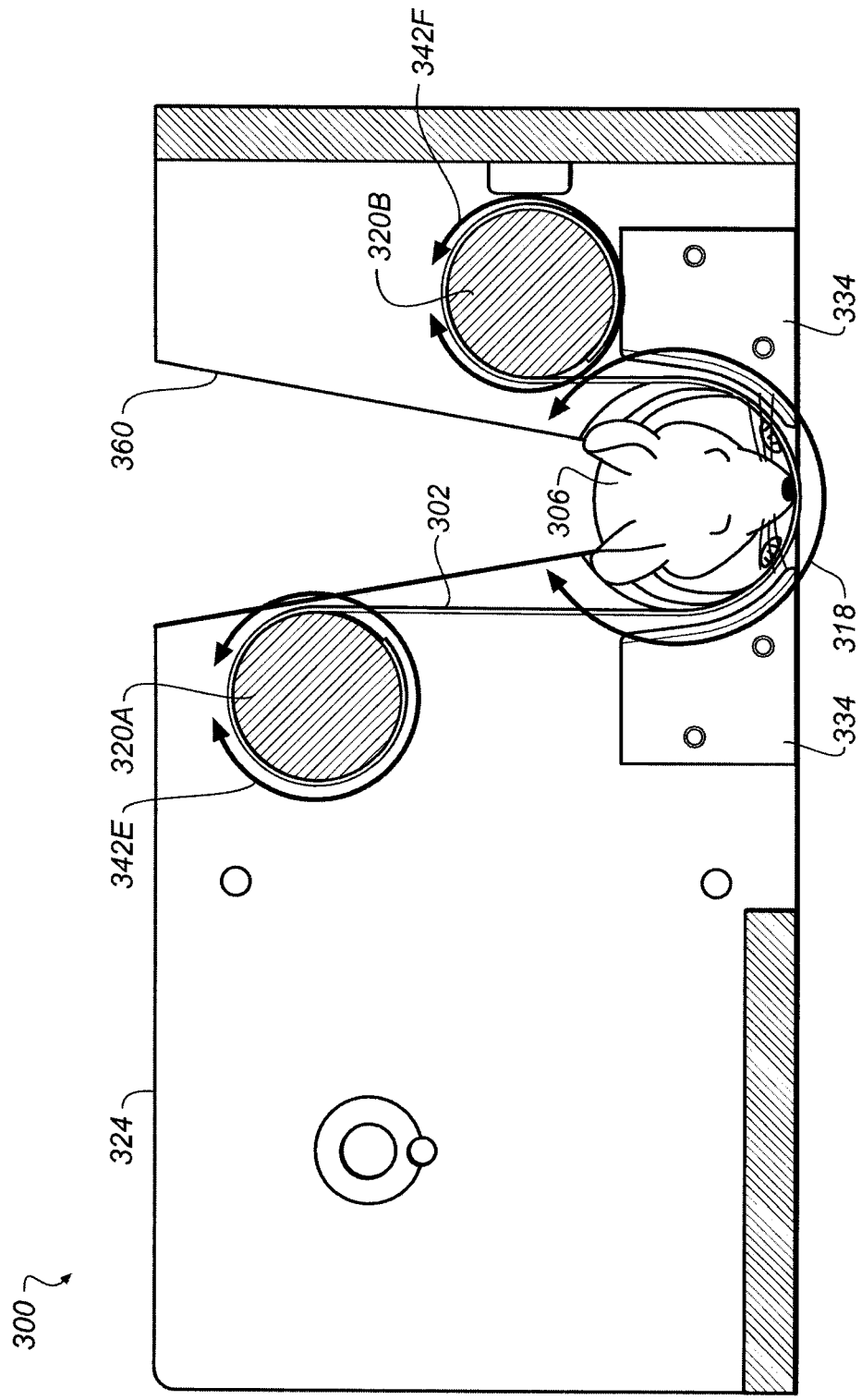
FIG. 5D shows a diagrammatic rear, sectional view of the torsional support apparatus of FIG. 2A where the animal is recumbent in a prone posture.
Figure 5E:
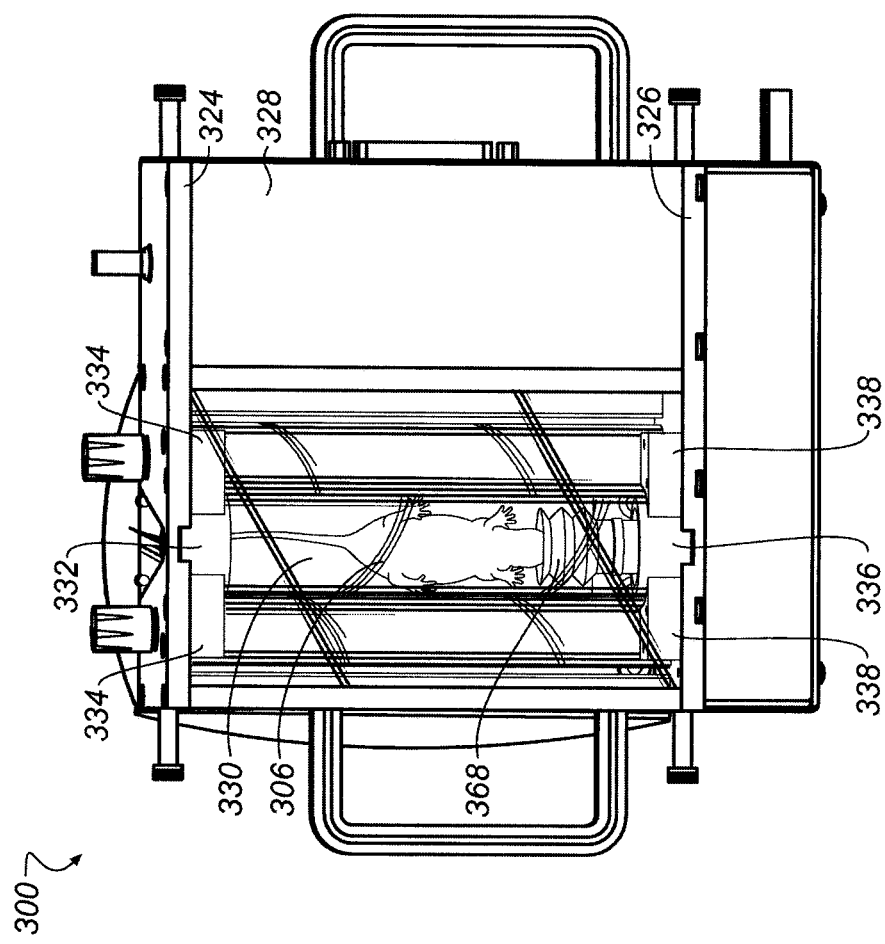
FIG. 5E shows a view from below the torsional support apparatus of FIG. 2A where the animal is recumbent in a prone posture.

FIGS. 2A and 2B show electronic imaging system 10, including a removable high-resolution phosphor screen 32, such as described in the previously mentioned application of Vizard et al, but configured in accordance with the present invention with a torsional support apparatus 300 inside sample environment 14. Alternatively, a high-sensitivity phosphor screen or a multiple panel phosphor screen may be used such as described in the previously mentioned application of Feke et al. Those skilled in the art will appreciate that system 10 may be reconfigured for imaging from above the animal or from any suitable angle, without departing from the present invention. Torsional support apparatus 300 includes an elongated, optically transparent flexible support member or film 302 that is mechanically constrained into an upwardly open, U-shaped loop 304, as shown in FIG. 3G. Film 302 has an axis of elongation and longitudinally extending edges 302a, 302b, as shown in FIG. 3C. A recumbent animal 306, such as a mouse, is positioned and constrained at the bottom of loop 304. Inhalational anesthesia, such as isoflurane, may be used to immobilize animal 306 and may be delivered to the animal from gas cylinders outside of system 10 through a hose 308a, which is attached to a gas port 310a in the wall of sample environment 14 at one end and to a hose barb 312a on torsional support apparatus 300 at the other end. Alternatively, the animal may be immobilized by an injectable anesthesia, such as ketamine. In addition, warm air may be delivered to maintain animal body temperature from a pump outside of system 10 through a hose 308b, which is attached to a gas port 310b in the wall of sample environment 14 at one end and to a hose barb 312b on torsional support apparatus 300 at the other end. Furthermore, gas may be exhausted by a pump outside of system 10 through a hose 308c, which is attached to a gas port 310c in the wall of sample environment 14 at one end and to a hose barb 312c on torsional support apparatus 300 at the other end. As will be described in more detail, torsional support apparatus 300 includes a belt drive 314, as shown in FIG. 3H, that is rotatable, as indicated by arrow 316 as shown in FIG. 5C to cause flexible support film 302 to move forward or backward, while maintaining loop 304 and rotating animal 306. Belt drive 314 can be commanded by communication and computer control system 26. Flexible support film 302 thereby can apply torsion to animal 306 within loop 304, causing animal 306 to undergo craniocaudal rotation, as indicated by arrow 318.

Figure 3A:
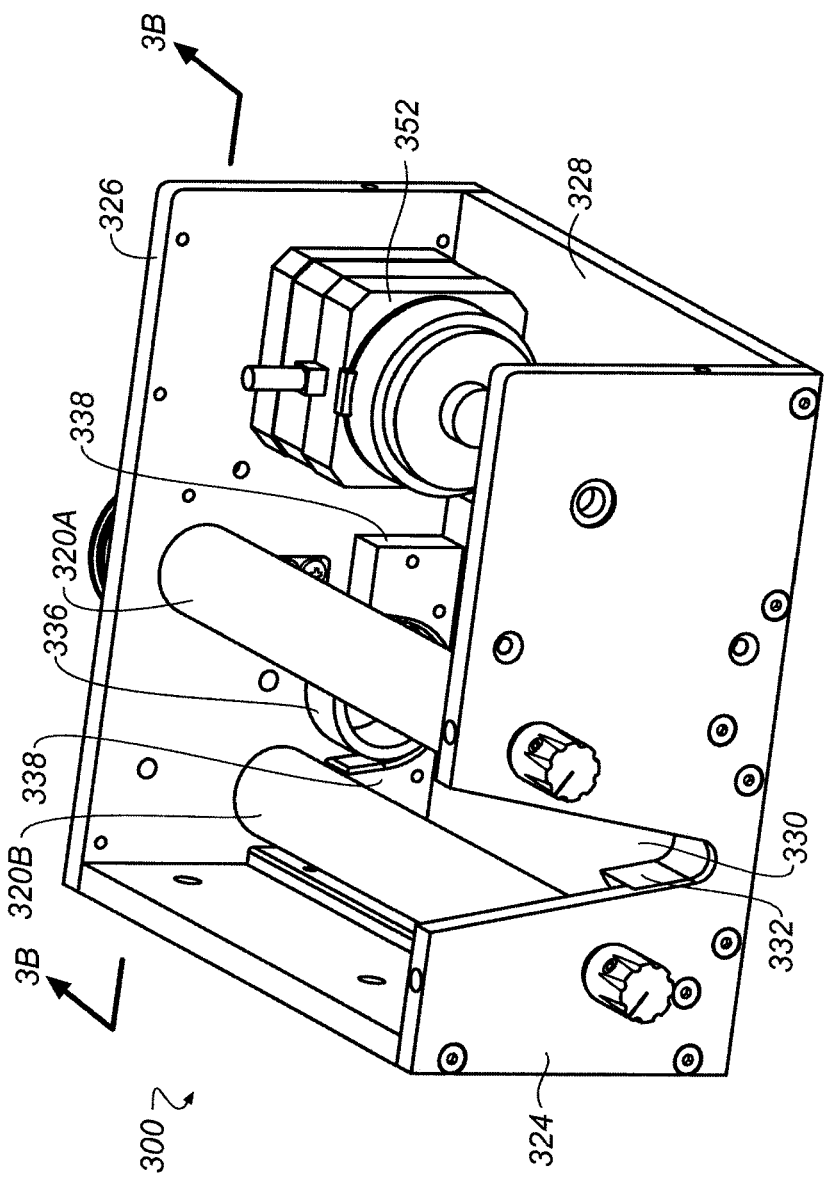
FIG. 3A shows a perspective, fragmentary view of the torsional support apparatus of FIG. 2A prior to installation of the support film.
Figure 3B:
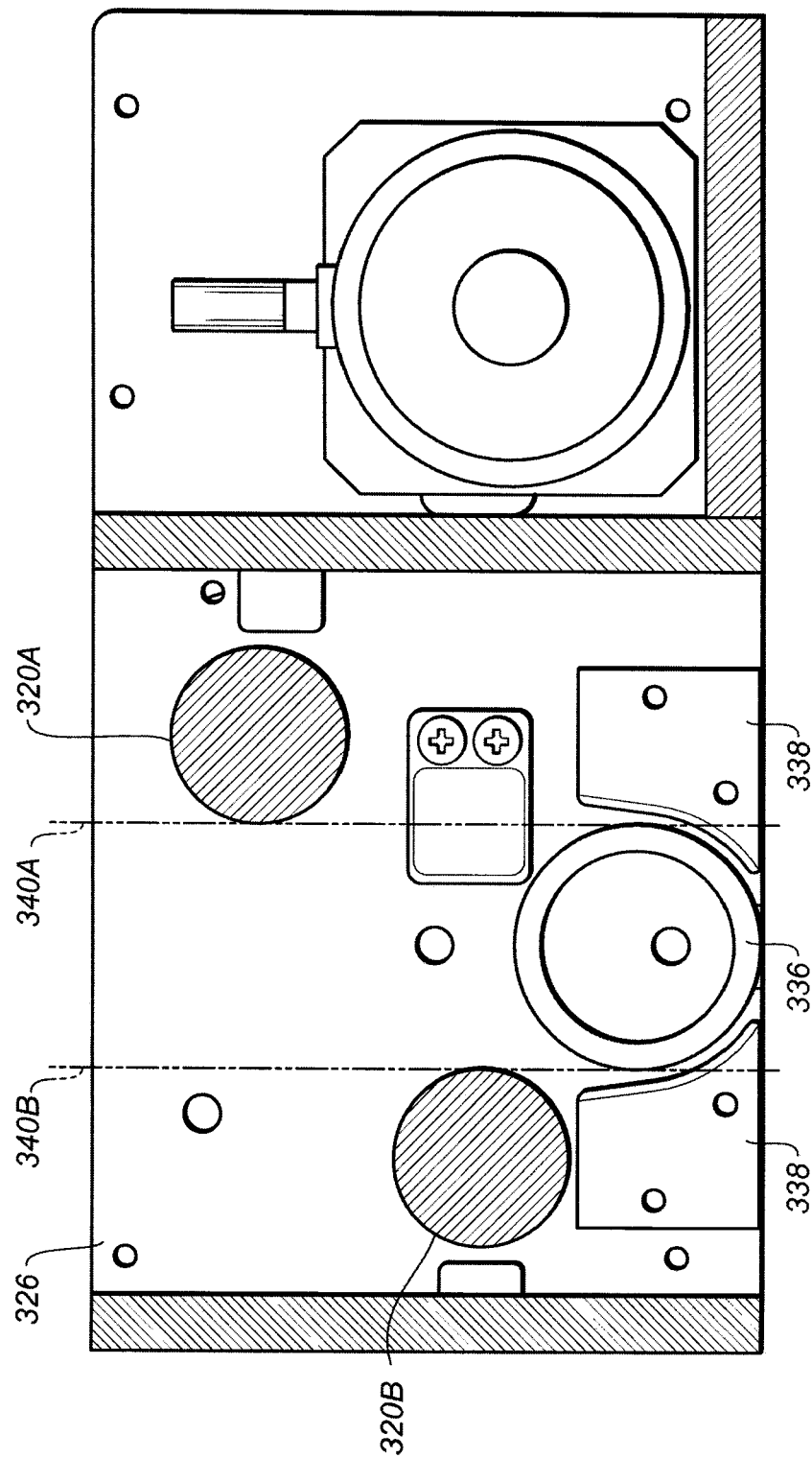
FIG. 3B shows a diagrammatic front, sectional view of the torsional support apparatus taken along line 3B-3B of FIG. 3A prior to installation of the support film.
Figure 3C:
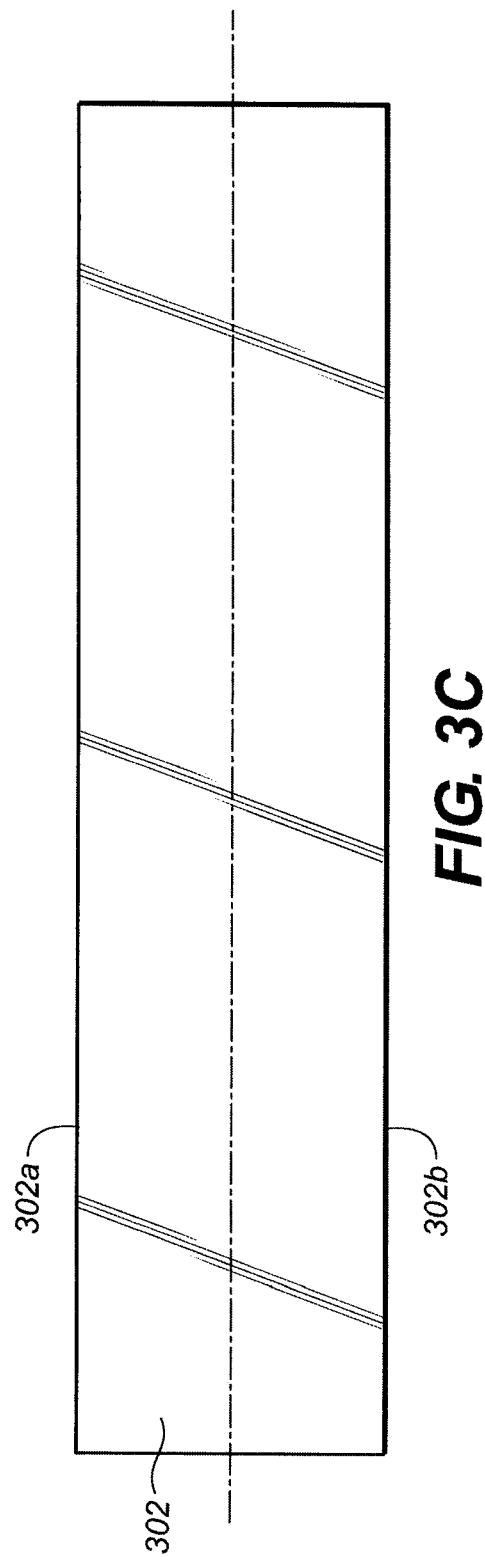
FIG. 3C shows a diagrammatic view of the support film in an unwound state.
Figure 3D:
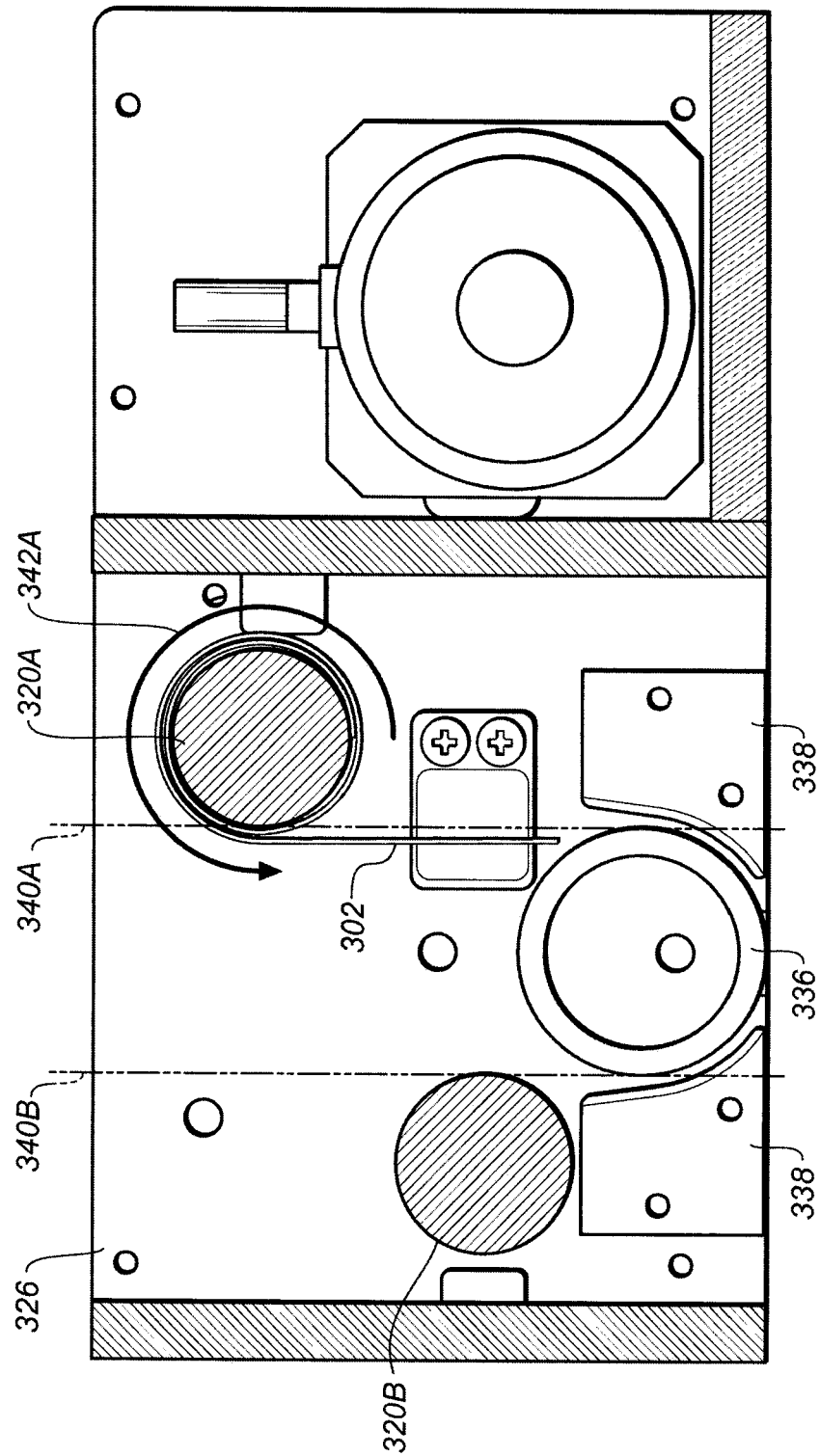
FIG. 3D shows a diagrammatic front, sectional view of the torsional support apparatus of FIG. 2A during installation of the support film.
Figure 3E:
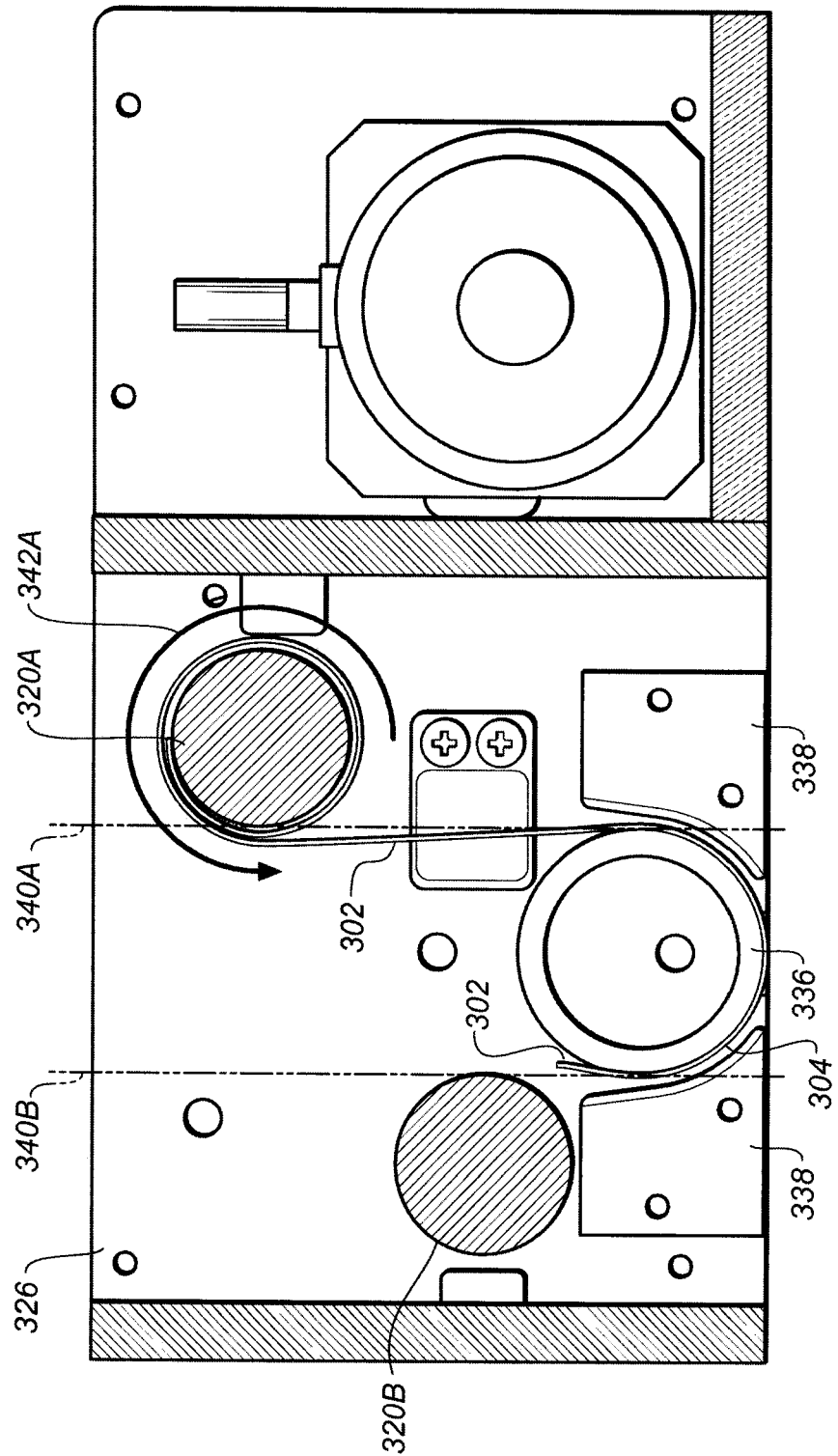
FIG. 3E shows a diagrammatic front, sectional view of the torsional support apparatus of FIG. 2A during installation of the support film.
Figure 3F:
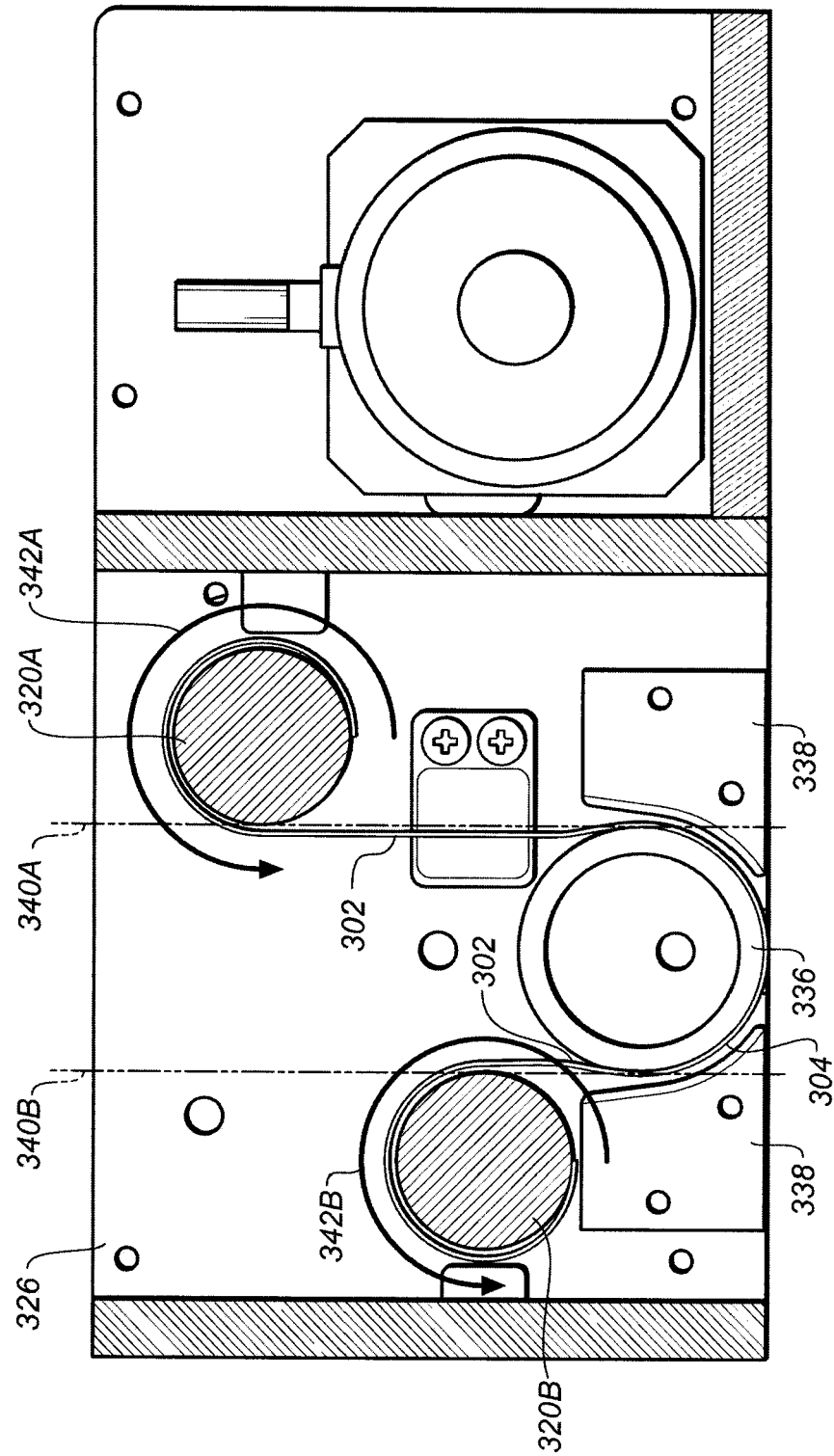
FIG. 3F shows a diagrammatic front, sectional view of the torsional support apparatus of FIG. 2A during installation of the support film.
Figure 3H:
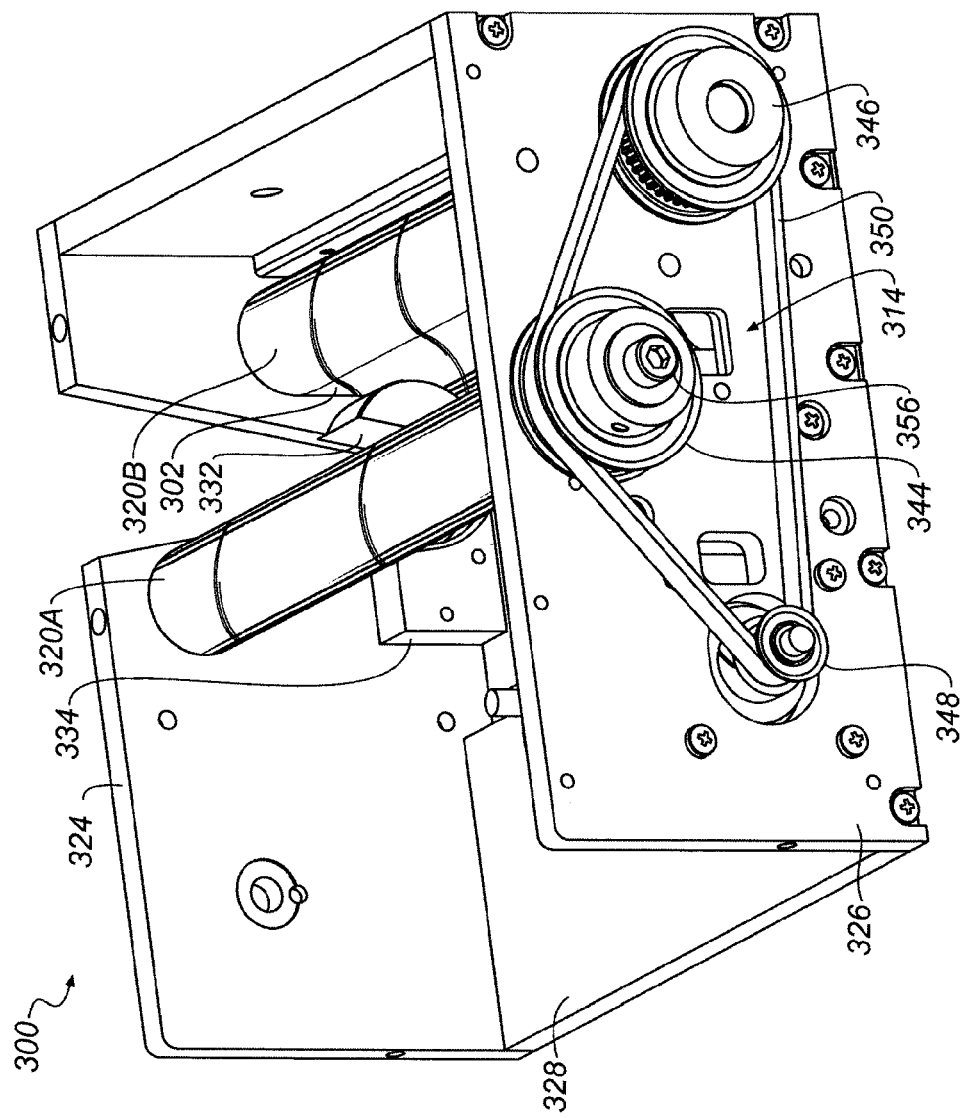
FIG. 3H shows a perspective, fragmentary view of the torsional support apparatus of FIG. 2A after installation of the support film.

FIGS. 3A-3H show the installation of flexible support film 302 into torsional support apparatus 300. FIGS. 3A and 3B show torsional support apparatus 300 prior to installation of flexible support film 302. Drive shafts 320A, 320B are equal in length, such length being chosen to be approximately equal to, or slightly greater than (but not less than), the length of animal 306, not including its tail. For example, a mouse having a mass 20 to 25 grams has a length of approximately 100 millimeters, not including the tail, therefore the length of drive shafts 320A, 320B is chosen to be 100 millimeters. Drive shafts 320A, 320B are mounted in a posterior bearing mount 324 at one end and an anterior bearing mount 326 at the other end. Posterior bearing mount 324 and anterior bearing mount 326 are rigidly mechanically coupled by a base plate 328 through which a window 330 has been cut. A posterior hub 332 and a posterior guide 334 are disposed in posterior bearing mount 324, as shown in FIG. 3H. An anterior hub 336 and an anterior guide 338 are disposed in anterior bearing mount 326. Posterior hub 332 and anterior hub 336 are cylindrical and have equal outer diameters and equal outer circumferences. The outer circumference of posterior hub 332 and anterior hub 336 is chosen to be approximate to the girth of animal 306. For example, a mouse having a mass 20 to 25 grams has a girth of approximately 90 millimeters, therefore the circumference of posterior hub 332 and anterior hub 336 is chosen to be 90 millimeters. For example, when using a support film 302 as described below with regard to FIG. 3C, mice having weights of 17 to 48 grams were accommodated by hubs 332, 336 having a diameter of about 29 mm, with no substantial slippage during rotation of the mouse. A hub diameter of about 32 mm accommodated mice having weights of about 23 to 48 grams. A hub diameter of about 35 mm accommodated mice having weights of about 48 grams. Those skilled in the art will appreciate that hubs of different diameters may be used interchangeably without departing from the scope of the present invention. Drive shafts 320A, 320B, respectively, are positioned horizontally with respect to posterior and anterior hubs 332 and 336 such that, as shown in FIG. 3B, the circumference of each is tangent to imaginary vertical planes 340A, 340B, respectively, which are oppositely tangent to one or the other side, respectively, of both posterior and anterior hubs 332 and 336. Drive shafts 320A, 320B are positioned vertically above base plate 328 so that they are sufficiently high to avoid obstruction of illumination projected through window 330 from below at an angle, for example a 45 degree angle, onto the ventral semigirth of animal 306, yet sufficiently low to be disposed under the ceiling of sample environment 14. The vertical positions of drive shafts 320A, 320B with respect to base plate 328 may or may not be equal. Posterior hub 332 includes a central passage that is cut away so as to be open on its upper side to allow the tail of the animal to be threaded through. Anterior hub 336 includes a central passage to allow inhalational anesthesia to flow through. Posterior guide 334 and anterior guide 338 have curved surfaces with equal diameters providing equal U-shaped gaps between posterior hub 332 and anterior hub 336, respectively, with the U opening upwardly. The size of the gaps is selected to be somewhat larger than, for example twice as large as, the thickness of flexible support film 302. Posterior hub 332, anterior hub 336, the curved surface of posterior guide 334, and the curved surface of anterior guide 338, are coaxial. Drive shafts 320A, 320B, posterior bearing mount 324, posterior hub 332, posterior guide 334, anterior bearing mount 326, anterior hub 336, anterior guide 338, and base plate 328, may be made of any rigid material, such as hard metals, hard plastics, wood, etc., sufficient to provide mechanical integrity to the apparatus.

FIG. 3C shows optically transparent flexible support film 302 in an unwound state. The width of flexible support film 302 is approximately equal to, or slightly less than (but not greater than), the length of drive shafts 320A, 320B. The length of flexible support film 302 is chosen to be sufficient to provide craniocaudal rotation of animal 306 over a desired angular range. For example, for a mouse having a mass 20 to 25 grams, hence a girth of 90 millimeters, where an angular range of 360 degrees is desired, the length of flexible support film 302 is chosen to be the sum of 90 millimeters and the extra length necessary to achieve attachment to drive shafts 320A, 320B. Hence the range of craniocaudal rotation angles, and hence the range of view angles, is unlimited and continuous. Flexible support film 302 is sufficiently thin and made of sufficiently flexible material such that the minimum bend radius among the radii of drive shafts 320A, 320B, and posterior and anterior hubs 332 and 336, is larger than the minimum bend radius of flexible support film 302 as dependent upon the film thickness and material. Flexible support film 302 also, preferably, has negligible fluorescence. Flexible support film 302 also, preferably, is cleanable using common cleaning agents such as an aqueous solution of detergents.

An example of a suitable material for flexible support film 302 is optically transparent polycarbonate with thickness in the range of 0.1 to 0.25 millimeters. For example, a suitable film is Bayer's Makrofol DE1-1, which is 0.005 inch thick and has a gloss finish on both sides. Such a film has a coefficient of friction sufficient to avoid substantial slippage when the film is used with hub diameters and mouse weights as previously discussed. Those skilled in the art will appreciate that other optically transparent films may be used without departing from the scope of the invention. A cyclo-olefin polymer film commercially known as Zeonor Film also has been found to be suitable. Polyester film is expected to work also. Polycarbonate and cyclo-olefin polymer films are preferable because of their low fluorescence. Films having thicknesses in the range of 0.005 inch to 0.010 inch have been found to work. Thicknesses somewhat outside this range would also work well, depending on the minimum bend radius of the material. The film should have a minimum bend radius less than or equal to the lesser of the hub diameter and the shaft diameter, and the shaft diameter could always be increased to be as large as the hub diameter as needed. Those skilled in the art will appreciate that support films or elements having patterns of perforations, or being formed from screen or fabric also could be used without departing from the scope of the invention, though such macroscopic structures in the support could interfere somewhat with optical and x-ray imaging.

FIGS. 3D, 3E, 3F show flexible support film 302 being installed. As shown in FIG. 3D, flexible support film 302 is first attached to drive shaft 320A, for example by tape which is preferably black with negligible fluorescence, and rolled onto drive shaft 320A. Flexible support film 302 is then unrolled by rotation of drive shaft 320A, as indicated by arrow 342A, such that the free end of flexible support film 302 is approximately coplanar with imaginary vertical plane 340A and directed toward the gaps between anterior hub 336 and anterior guide 338 as shown in FIG. 3D and between posterior hub 332 and posterior guide 334 as shown in FIG. 3H. As shown in FIG. 3E, flexible support film 302 is next wound through the just-described gaps, thereby mechanically constraining flexible support film 302 into upwardly open, U-shaped loop 304. As shown in FIG. 3F, flexible support film 302 is next attached to drive shaft 320B, for example by tape which is preferably black with negligible fluorescence, and rolled onto drive shaft 320B by co-rotation of both drive shafts 320A, 320B, as indicated by arrows 342A and 342B. As shown in FIG. 3G, any slack in flexible support film 302 may be removed by counter-rotation of drive shafts 320A, 320B, as indicated by arrows 342C and 342D.

FIG. 3H shows torsional support apparatus 300 at the final step of film installation. Drive shafts 320A, 320B are shown to be inserted as shafts into pulleys 344 and 346, respectively, which are components in belt drive 314 which also includes a drive pulley 348 and a drive belt 350. Pulley 348 is mechanically coupled to the shaft of a stepper motor 352 disposed on the opposite side of posterior bearing mount 324 as shown in FIG. 3A. Pulley 344 includes set screw 356. After the slack in flexible support film 302 is removed, set screw 356 is secured into drive shafts 320A, thereby mechanically coupling drive shaft 320A to pulley 344. Hence, flexible support film 302 is tightly wound in torsional support apparatus 300 to define U-shaped loop 304. The rounded bottom of U-shaped loop 304 has an inner diameter equal to the outer diameter of hubs 332 and 334 and is coaxial with hubs 332 and 334.

Figure 4:
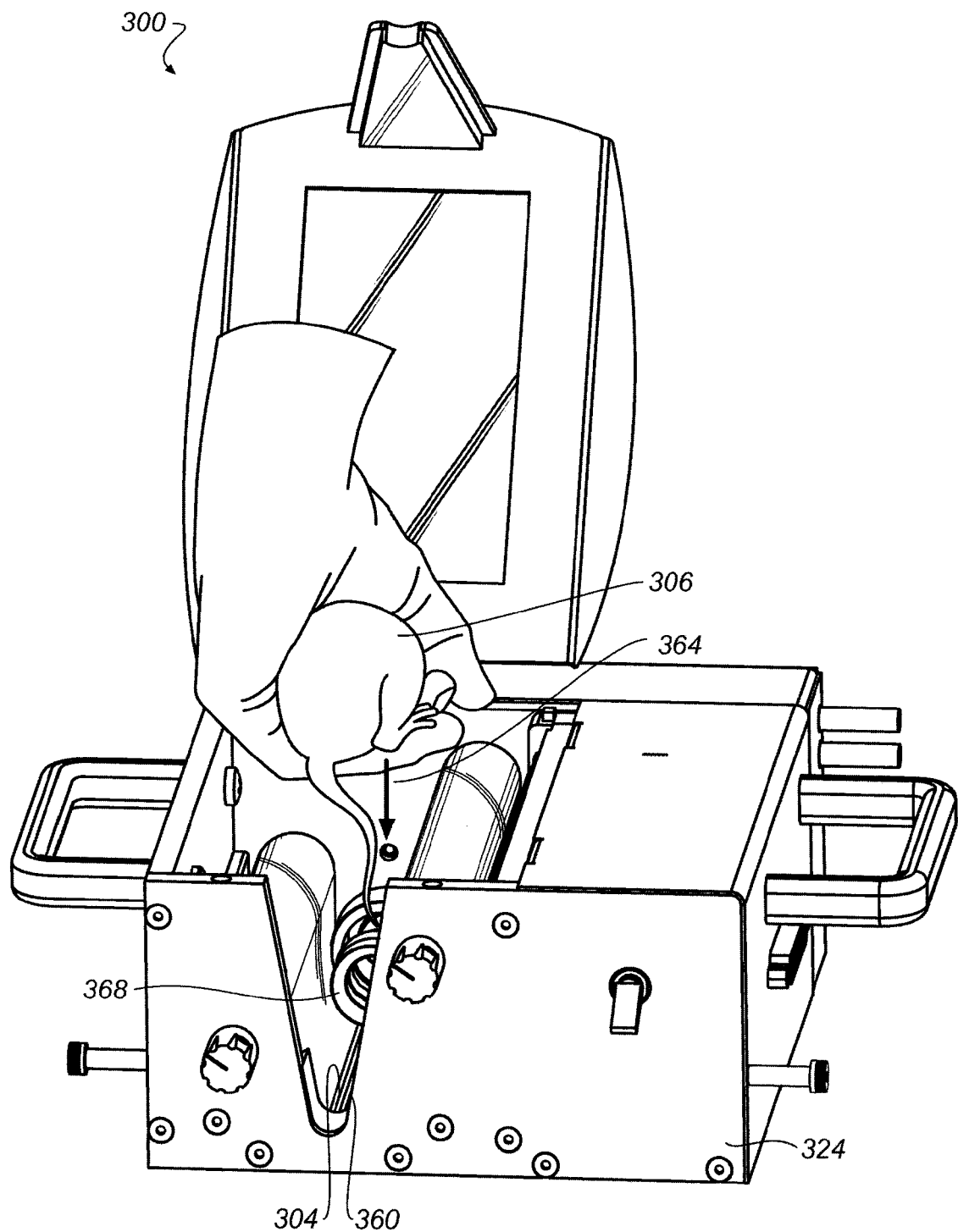
FIG. 4 shows a perspective view from above of the torsional support apparatus of FIG. 2A during loading of the animal.

FIG. 4 shows torsional support apparatus 300 during loading of animal 306. While animal 306 is under the effects of anesthesia, for example an injectable anesthesia or by recent exposure to inhalational anesthesia, the human experimenter lowers animal 306 down into U-shaped loop 304, as indicated by arrow 364. The nose of animal 306 may be inserted into an open end of an anterior expandable tubing segment 368, to enable administration of anesthesia flowing from hose 308a, as well as to stabilize the longitudinal position of animal 306. The tail of animal 306 may extend through cut-out 360 in posterior bearing mount 324 and posterior hub 332. Hence the human experimenter has access from above to animal 306. For example, the experimenter may perform intimate delivery, such as by injection, oral gavage, inhalation, transrectal delivery, transdermal delivery, or transmucosal delivery, of a substance, such as a drug, optical fluorescence imaging agent, X-ray contrast agent, or radionuclide imaging agent, to animal 306, where it is desirable to capture images of animal 306 both prior to and after delivery of the substance without substantially physically disturbing animal 306 in electronic imaging system 10 and especially desirable when studying the perfusion and clearance of imaging or contrast agents or therapeutic response of a drug over time. The human experimenter has access to the immediate environment around animal 306, for example, when it is desirable to clean the immediate environment of residue, including animal urine, feces, or surface debris, that might otherwise cause imaging artifacts. Minimal manipulation of animal 306 is required to place it in electronic imaging system 10 in a desired posture, hence facilitating an ergonomic protocol for the human experimenter. Recumbent postures are used to minimize physiological stress on animal 306.

FIGS. 5A-5E show torsional support apparatus 300 and removable high-resolution phosphor screen 32 where animal 306 is recumbent in a prone posture. Anterior expandable tubing segment 368 extends from within the hollow interior of anterior hub 336. Inhalational anesthesia is shown to be delivered through hose barb 312a, then inside anterior bearing mount 326, eventually into anterior expandable tubing segment 368, whereby anterior expandable tubing segment 368 is sufficiently expanded to extend to the head of animal 306. An example of a commercially available material suitable for anterior expandable tubing segment is 15 mm inner diameter expandable tubing with 3:1 compressed/expanded ratio from GlobalMed Inc. Alternatively, an injectable anesthesia may be used.

The craniocaudal axis of animal 306 is approximately coaxial with the rounded bottom of U-shaped loop 304. Because flexible support film 302 is mechanically constrained by hubs 332 and 336, the semi-circumference of the rounded bottom of U-shaped loop 304 is approximately equal to the semi-girth of animal 306, so that recumbent animal 306 is in contact with flexible support film 302 approximately throughout the animal's semigirth. Communication or computer control system 26 controls stepper motor 352 to cause rotation of pulley 348, as indicated by arrow 316, thereby operating belt drive 314 and causing pulleys 344 and 346 to rotate. Because pulleys 344 and 346 are mechanically coupled to drive shafts 320A, 320B, respectively, drive shafts 320A, 320B are caused to rotate, as indicated by arrows 342E, 342F. Because flexible support film 302 is attached to drive shafts 320A, 320B and tightly wound, flexible support film 302 is caused to move through U-shaped loop 304 defined by the mechanical constraints of flexible support film 302. Because animal 306 is in contact with U-shaped loop 304 approximately throughout its semigirth, movement of flexible support film 302 applies torsion to animal 306, causing animal 306 to undergo craniocaudal rotation, as indicated by arrow 318.

Figure 6A:
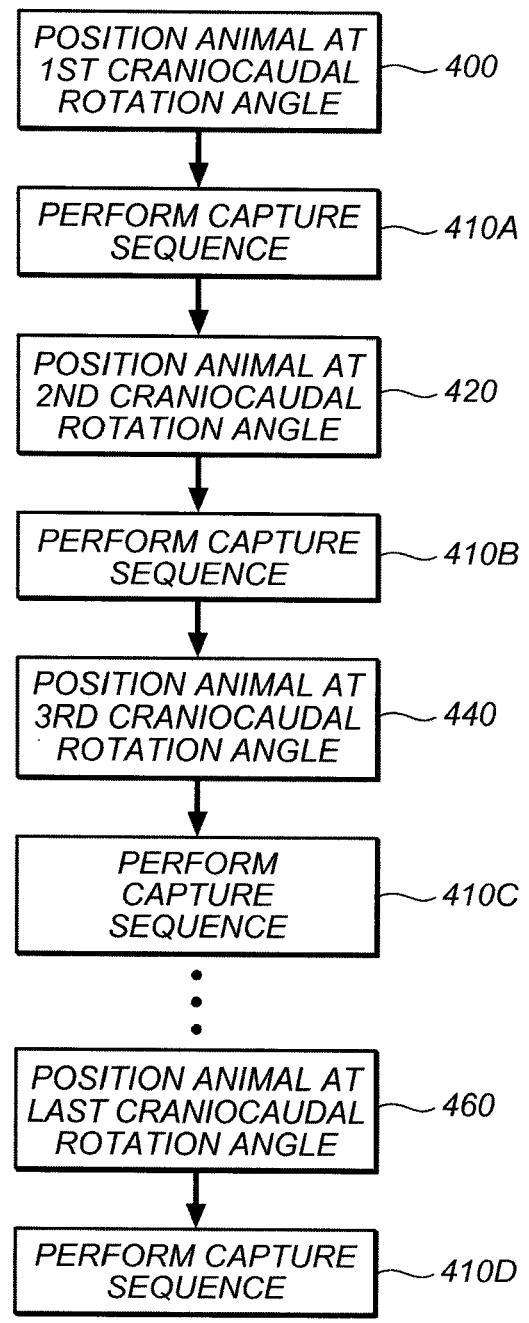
FIG. 6A shows an overall workflow diagram for craniocaudal rotation of an animal in accordance with a method of the present invention.
Figure 6B:
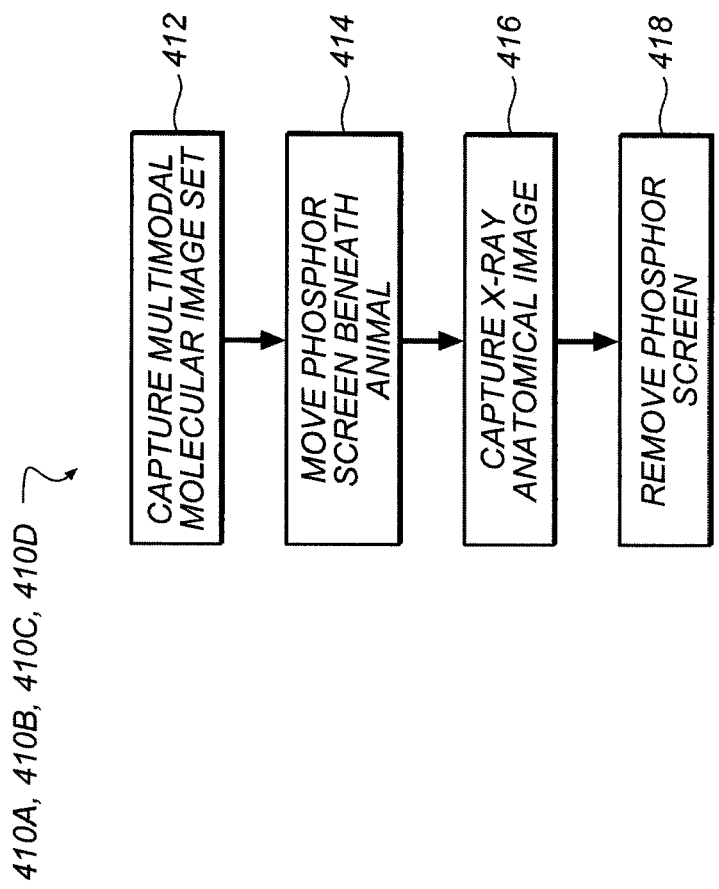
FIG. 6B shows a workflow diagram in accordance with a method of the present invention.
Figure 6C:
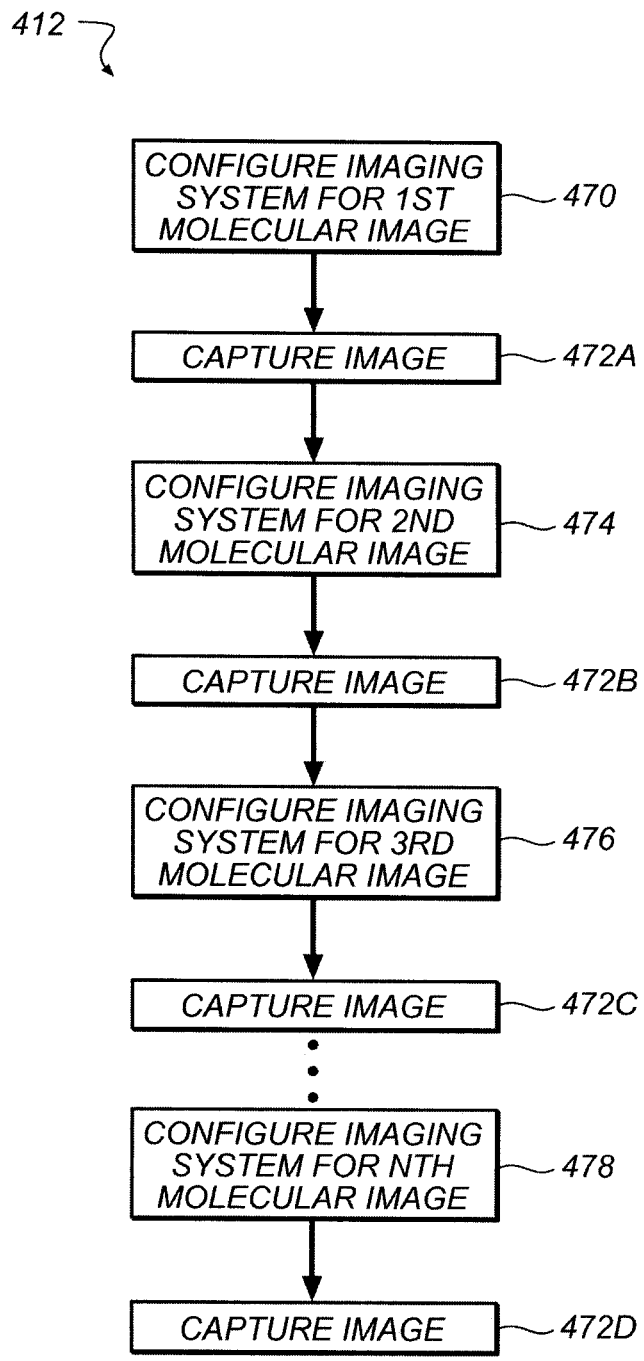
FIG. 6C shows a workflow diagram in accordance with a method of the present invention.

FIGS. 6A-6C show workflow diagrams in accordance with a method of the present invention. FIG. 6A shows the overall workflow diagram for craniocaudal rotation of animal 306. First, animal 306 is placed in U-shaped loop 304, as previously described. Then the animal is positioned by torsional support apparatus 300 at a first desired craniocaudal rotation angle in step 400. Next, electronic imaging system 10 performs a capture sequence in step 410A. Next, animal 306 is positioned by torsional support apparatus 300 at a second desired craniocaudal rotation angle in step 420. Next, electronic imaging system 10 performs another capture sequence in step 410B. Next, animal 306 is positioned by torsional support apparatus 300 at a third desired craniocaudal rotation angle in step 440. Next, electronic imaging system 10 performs another capture sequence in step 410C. Animal 306 is positioned by torsional support apparatus 300 at as many different craniocaudal rotation angles as desired, and electronic imaging system 10 performs capture sequences for each craniocaudal rotation angle, until animal 306 is positioned by torsional support apparatus 300 at the last craniocaudal rotation angle in step 460; and electronic imaging system 10 performs the last capture sequence in step 410D. The distribution of the different craniocaudal rotation angles within the range of rotation may be either periodic or arbitrary. The rotation direction between successive angles may be either constant, whether clockwise or counterclockwise, or may be arbitrary.

FIG. 6B shows a preferred embodiment of the workflow diagram for steps 410A, 410B, 410C, 410D. First, electronic imaging system 10 acquires a multimodal molecular image set in step 412. Molecular imaging modes may include optical imaging modes such as fluorescence and luminescence modes, and also radioactive isotope imaging mode whereby application of a second phosphor screen or panel optimized for high-sensitivity is preferable. Second, high-resolution phosphor screen 32 is moved into position under animal 306 in step 414. Third, electronic imaging system 10 acquires an X-ray anatomical image in step 416. Last, high-resolution phosphor screen 32 is removed from beneath animal 306 in step 418. Alternatively, steps 410A, 410B, 410C, and 410D may exclude steps 414, 416, and 418, and include only step 412. Alternatively, high-resolution phosphor screen may be fixed in place beneath animal 306 and steps 410A, 410B, 410C, and 410D may exclude steps 412, 414, and 418, and include only step 416.

FIG. 6C shows the workflow diagram for step 412. First, electronic imaging system 10 is configured for a first molecular image in step 470. Next, electronic imaging system 10 captures an image in step 472A. Next, electronic imaging system 10 is configured for a second molecular image in step 474. Next, electronic imaging system 10 captures another image in step 472B. Next, electronic imaging system 10 is configured for a third molecular image in step 476. Next, electronic imaging system 10 captures another image in step 472C. Electronic imaging system 10 is configured for and captures as many different molecular images as desired, until electronic imaging system 10 is configured for the last molecular image in step 478 and captures the last image in step 472D. The different configurations of electronic imaging system 10 may involve selection of different excitation and emission wavelengths, toggling illumination on or off, and installation or removal of a second high-sensitivity phosphor screen or panel for radioactive isotope imaging.

Figure 7A:
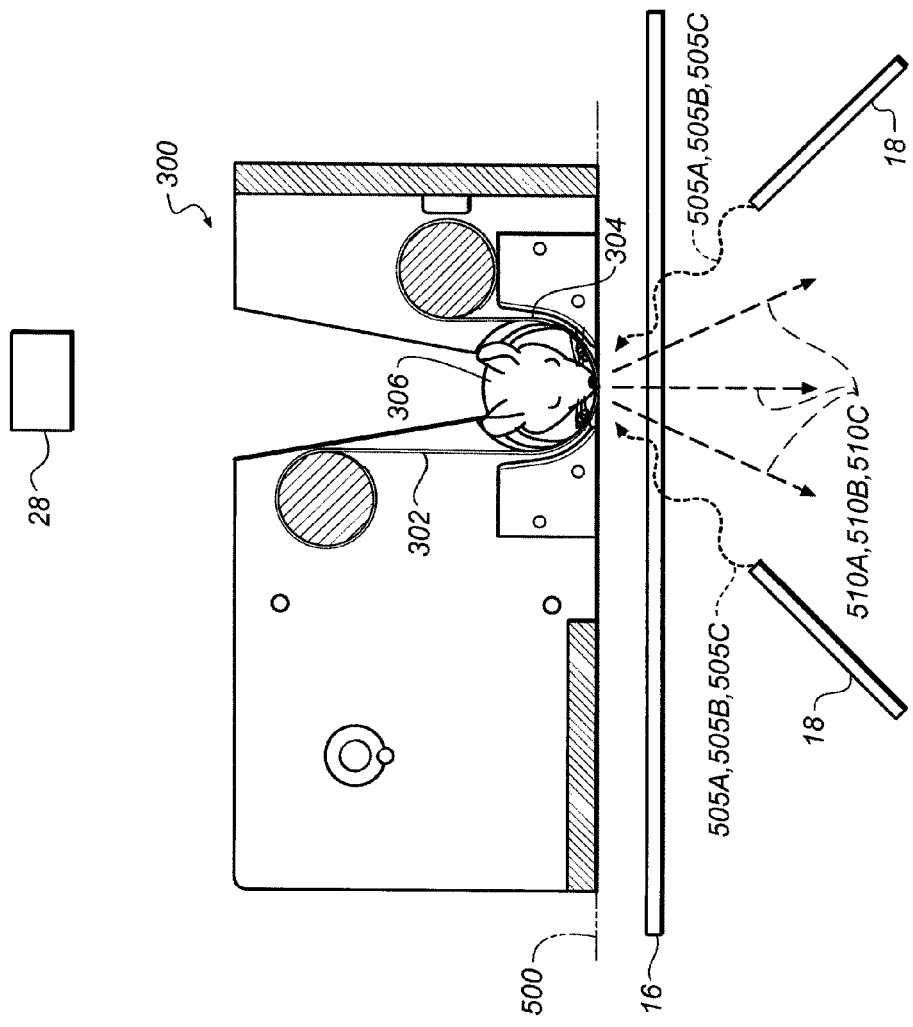
FIG. 7A shows a diagrammatic rear view of the torsional support apparatus and removable high-resolution phosphor screen of FIG. 2A where the animal has undergone craniocaudal rotation to a prone posture, the high-resolution phosphor screen has been removed, and the animal is being imaged using an optical imaging mode.
Figure 7A:
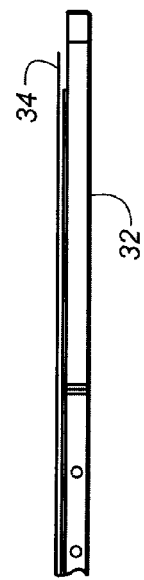
Figure 8A:
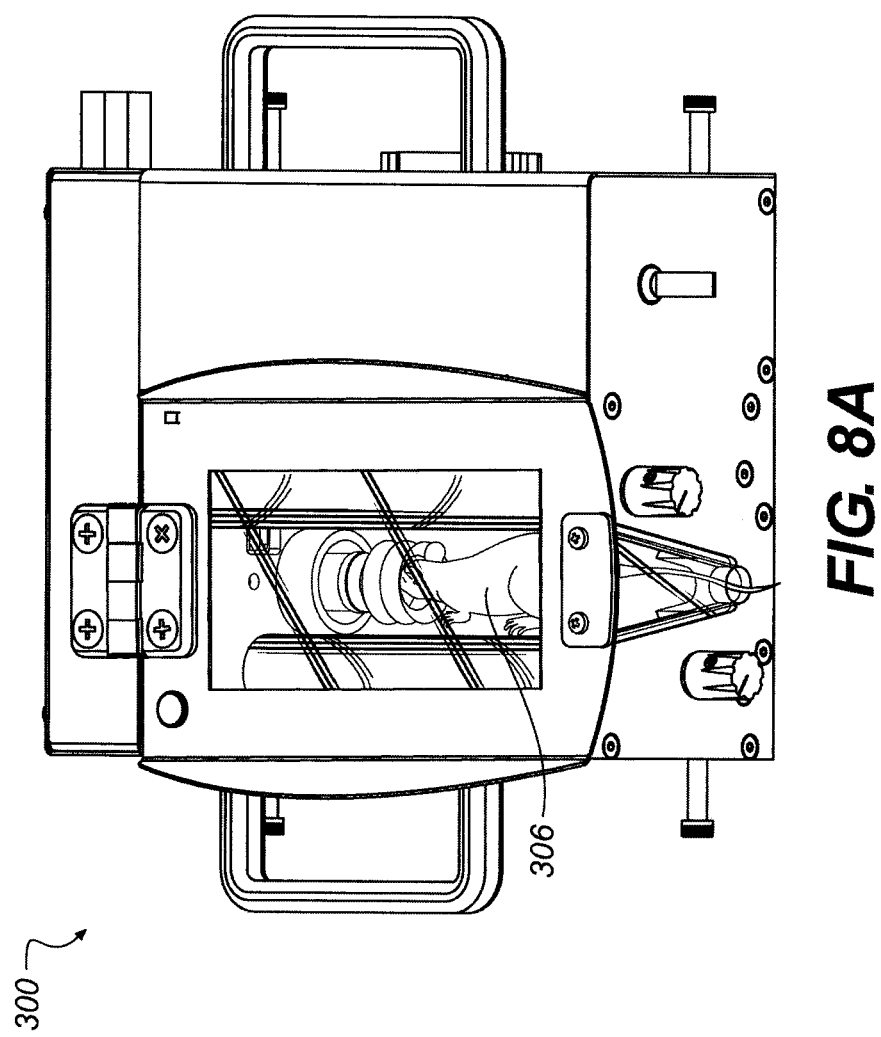
FIG. 8A shows a perspective view from the front of the torsional support apparatus of FIG. 2A where the animal has underwent craniocaudal rotation to an obliquely recumbent posture.
Figure 8B:
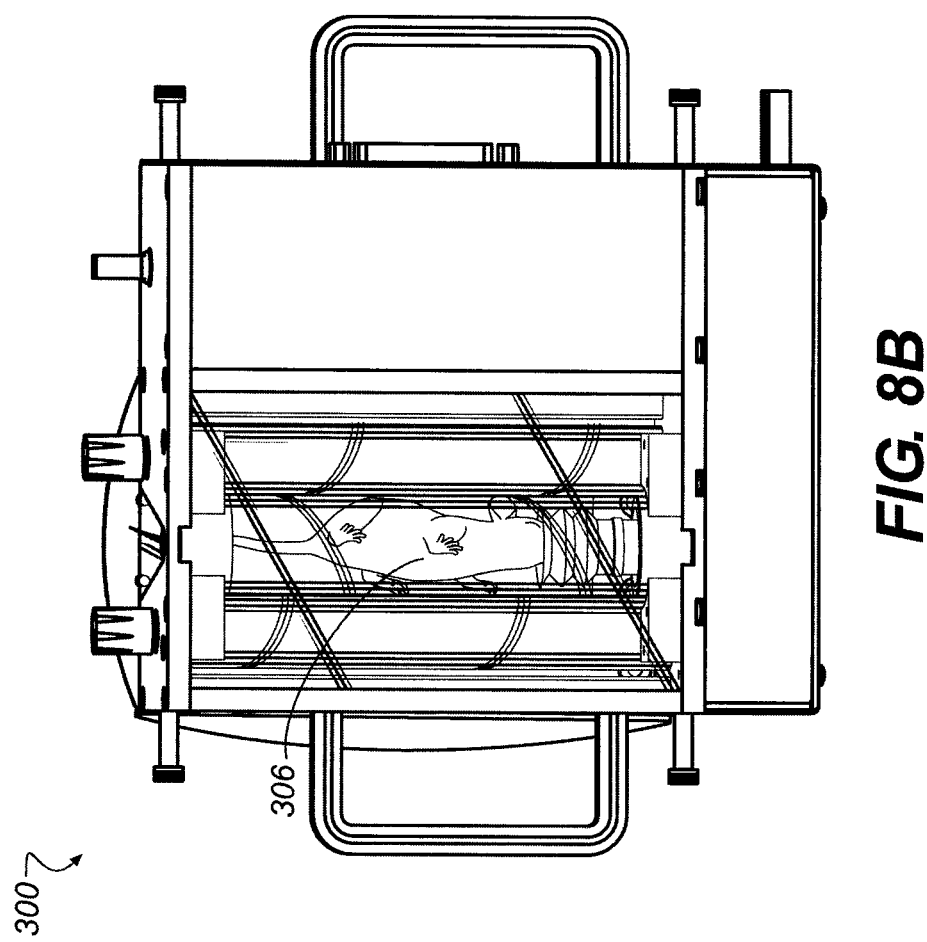
FIG. 8B shows a view from below the torsional support apparatus of FIG. 2A where the animal has underwent craniocaudal rotation to an obliquely recumbent posture.
Figure 8C:
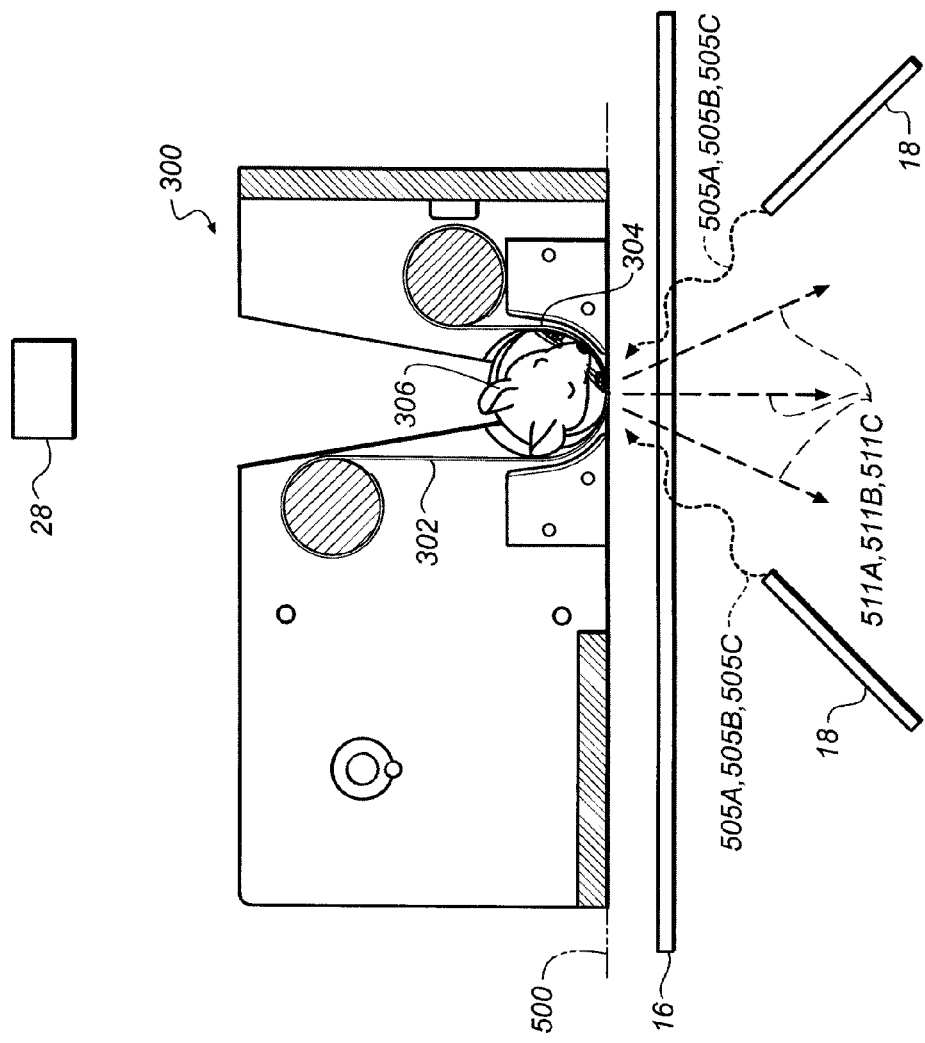
FIG. 8C shows a diagrammatic rear view of the torsional support apparatus and removable high-resolution phosphor screen of FIG. 2A where the animal has underwent craniocaudal rotation to an obliquely recumbent posture, the high-resolution phosphor screen has been removed, and the animal is being imaged using an optical imaging mode.
Figure 8C:
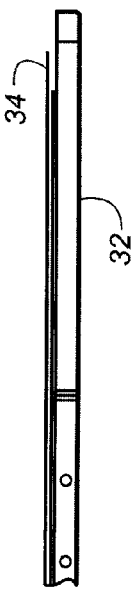
Figure 8D:
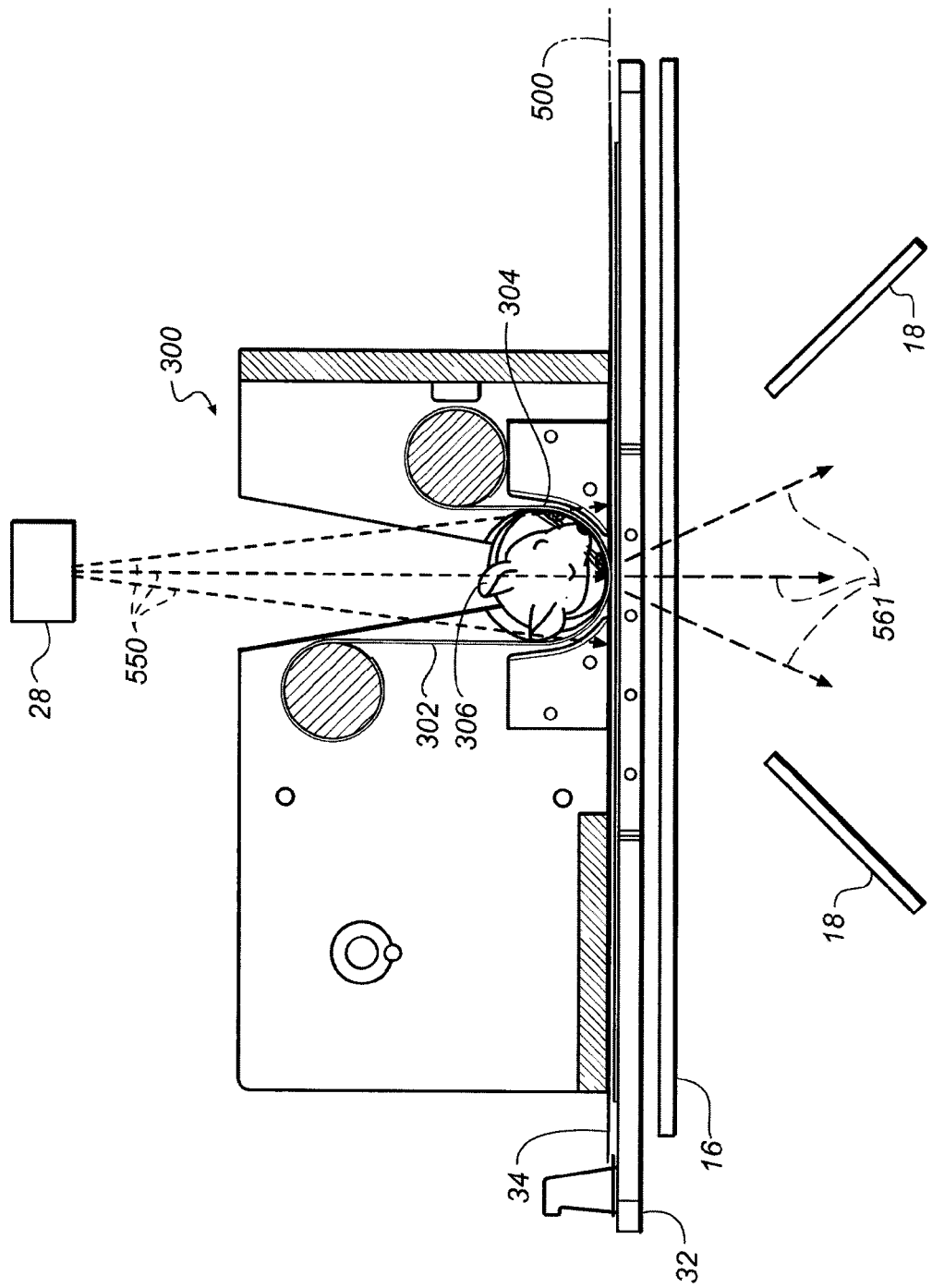
FIG. 8D shows a diagrammatic rear view of the torsional support apparatus and removable high-resolution phosphor screen of FIG. 2A where the animal has underwent craniocaudal rotation to an obliquely recumbent posture, the high-resolution phosphor screen has been installed, and the animal is being imaged using an X-ray imaging mode.
Figure 9A:
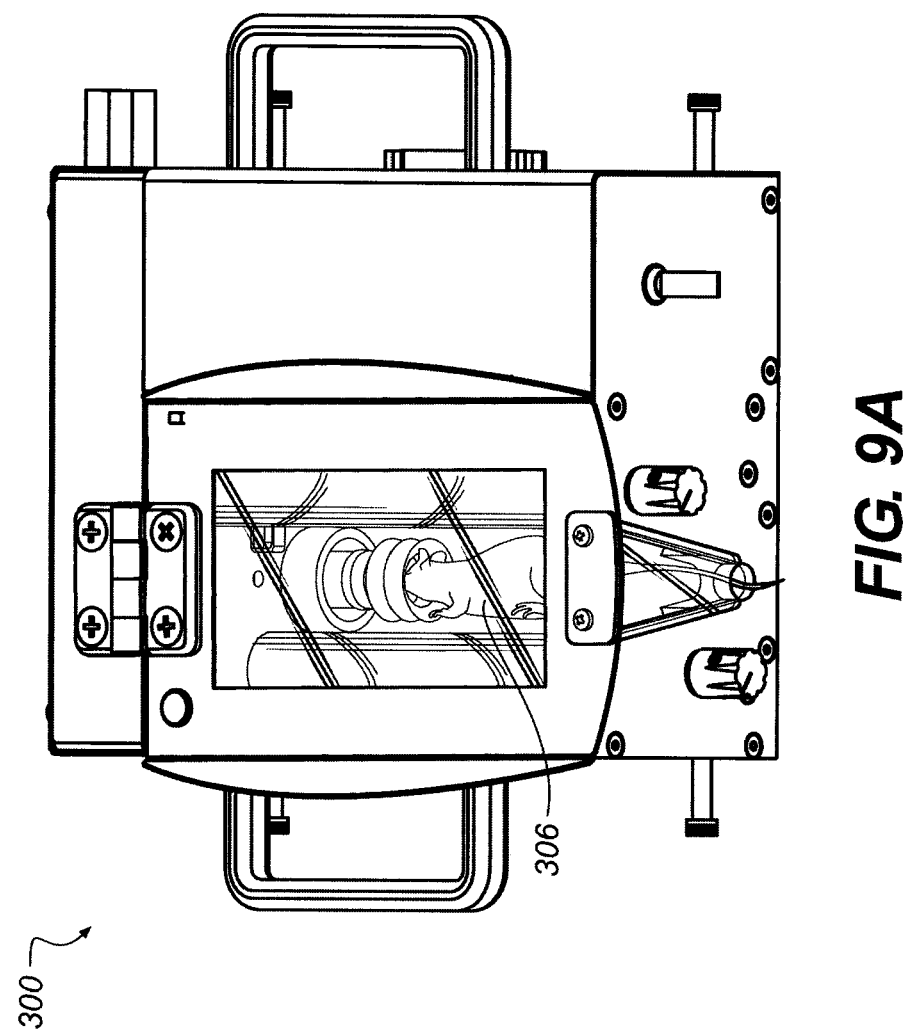
FIG. 9A shows a perspective view from the front of the torsional support apparatus of FIG. 2A where the animal has underwent craniocaudal rotation to a laterally recumbent posture.
Figure 9B:
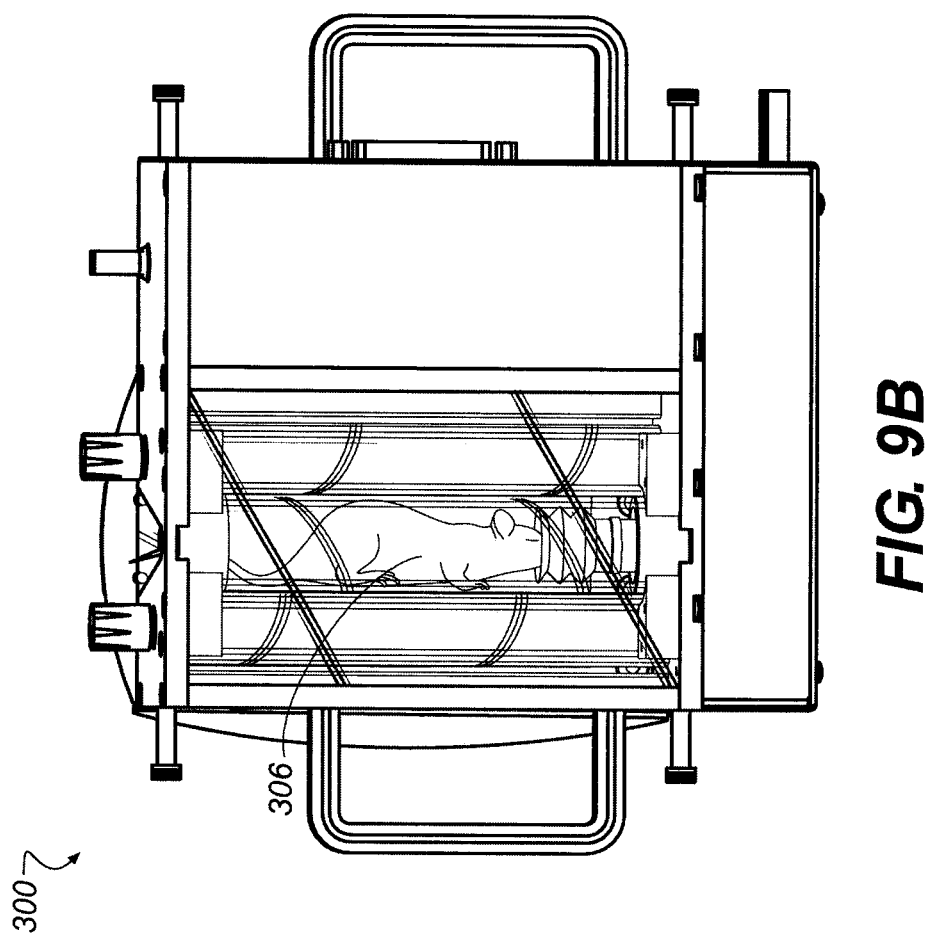
FIG. 9B shows a view from below the torsional support apparatus of FIG. 2A where the animal has underwent craniocaudal rotation to a laterally recumbent posture.
Figure 9C:
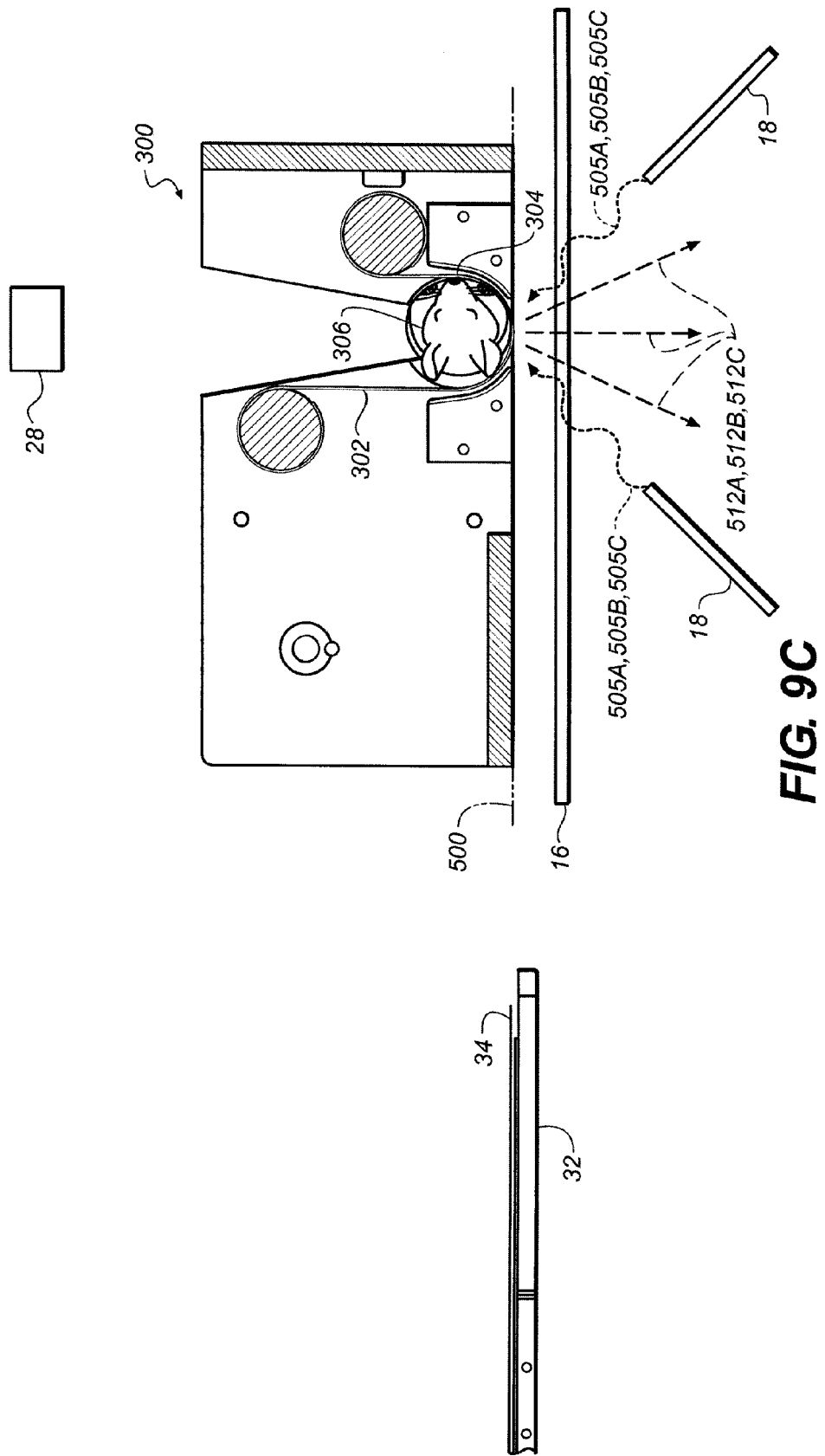
FIG. 9C shows a diagrammatic rear view of the torsional support apparatus and removable high-resolution phosphor screen of FIG. 2A where the animal has underwent craniocaudal rotation to a laterally recumbent posture, the high-resolution phosphor screen has been removed, and the animal is being imaged using an optical imaging mode.

FIGS. 7A, 7B show torsional support apparatus 300 and removable high-resolution phosphor screen 32 during steps 400 and 410A. Torsional support apparatus 300 is horizontally positioned directly under microfocus X-ray source 28. FIG. 7A shows torsional support apparatus 300 and removable high-resolution phosphor screen 32 where animal 306 has undergone craniocaudal rotation to a prone posture during step 400, high-resolution phosphor screen 32 has not been moved beneath animal 306, and a molecular image set of animal 306 is being captured in step 412 by electronic imaging system 10 configured for an optical molecular imaging mode, such as the illustrated fluorescence mode. Excitation light of three different wavelengths 505A, 505B, 505C is sequentially projected in an epi-illumination configuration by fiber optics 18 onto the ventral semigirth of animal 306, over its entire length, for configuration steps 470, 474, 476. Alternatively, excitation light could be provided in a trans-illumination configuration, not shown, onto the dorsal semigirth of the animal, over its entire length. Alternative means for providing excitation light include, but are not limited to, laser scanning and structured illumination, such as disclosed in the previously mentioned application of Feke. Emission light 510A, 510B, 510C is emitted from animal 306 in fluorescent response to excitation light 505A, 505B, 505C and is captured in capture steps 472A, 472B, 472C by electronic imaging system 10. Lens and camera system 24 is focused on focal plane 500, which is horizontal and tangent to the round bottom of U-shaped loop 304. The round bottom of U-shaped loop 304 provides a physical surface to serve as a reference for focal plane 500 for lens and camera system 24 to facilitate the capture of sharp, well-resolved images. As an alternative example, emission light 510A, 510B, 510C may instead be luminescence from within animal 306 without excitation light.

FIG. 7B shows torsional support apparatus 300 when removable high-resolution phosphor screen 32 has been moved beneath animal 306 during step 414 and an X-ray anatomical image of animal 306 is being captured in step 416 by electronic imaging system 10 configured for X-ray mode. High-resolution phosphor sheet 34 is coplanar with focal plane 500. X-rays 550 are emitted by microfocus X-ray source 28 toward animal 306 and penetrate animal 306 depending upon the attenuation of the animal's soft and skeletal tissue. X-rays 550 then intercept high-resolution phosphor sheet 34 which responds by emitting phosphorescent visible light 560 that is captured in capture step 416 by electronic imaging system 10 wherein lens and camera system 24 is focused on focal plane 500. Hence optically transparent flexible support film 302 facilitates multimodality imaging in that high-resolution removable phosphor screen 32 can be located proximally to, specifically tangent to, the support surface, thereby providing a common focal plane 500 for both the optical imaging modes (bright-field mode, fluorescence mode, and luminescence mode) and the imaging modes requiring a phosphor screen (X-ray mode and radioactive isotope mode). Common focal plane 500 is necessary for precise co-registration of overlaid images from the optical imaging modes and the imaging modes requiring a phosphor screen. Also, the imaging light path is stationary and common for all view angles and all imaging modes, thereby providing for simple, inexpensive components, specifically platen 16, mirror 22, and lens and camera system 24, to define the imaging light path.

FIGS. 8A-8D show torsional support apparatus 300 and removable high-resolution phosphor screen 32 during steps 420 and 410B, where animal 306 has undergone craniocaudal rotation by 45 degrees from the prone posture to an obliquely recumbent posture. Screen 32 has been removed from beneath animal 306 in FIGS. 8A, 8B and 8C, then moved beneath animal 306 in FIG. 8D. The same configuration of electronic imaging system 10 and the same workflow that were applied as shown and described for FIGS. 7A, 7B are applied in FIGS. 8A, 8B, 8C and 8D. Electronic imaging system 10 captures a different molecular image set of animal 306 by imaging emission light 511A, 511B, 511C, and a different X-ray anatomical image of animal 306 by imaging phosphorescence 561, due to the craniocaudal rotation of animal 306.

FIGS. 9A-9D show torsional support apparatus 300 and removable high-resolution phosphor screen 32 during steps 440 and 410C, where animal 306 has undergone craniocaudal rotation by an additional 45 degrees from the obliquely recumbent posture to a laterally recumbent posture. The same configuration of electronic imaging system 10 and the same workflow that were applied as shown and described for FIGS. 7A, 7B are applied in FIGS. 9A, 9B, 9C and 9D. Electronic imaging system 10 captures a different molecular image set of animal 306 by imaging emission light 512A, 512B, 512C, and a different X-ray anatomical image of animal 306 by imaging phosphorescence 562, due to the additional craniocaudal rotation of animal 306. Animal 306 may undergo further craniocaudal rotation steps and electronic imaging system 10 may be repeatedly configured to capture molecular and X-ray images of animal 306 as desired, even through a supine posture and all the way around and back to a prone posture.

Figure 10:
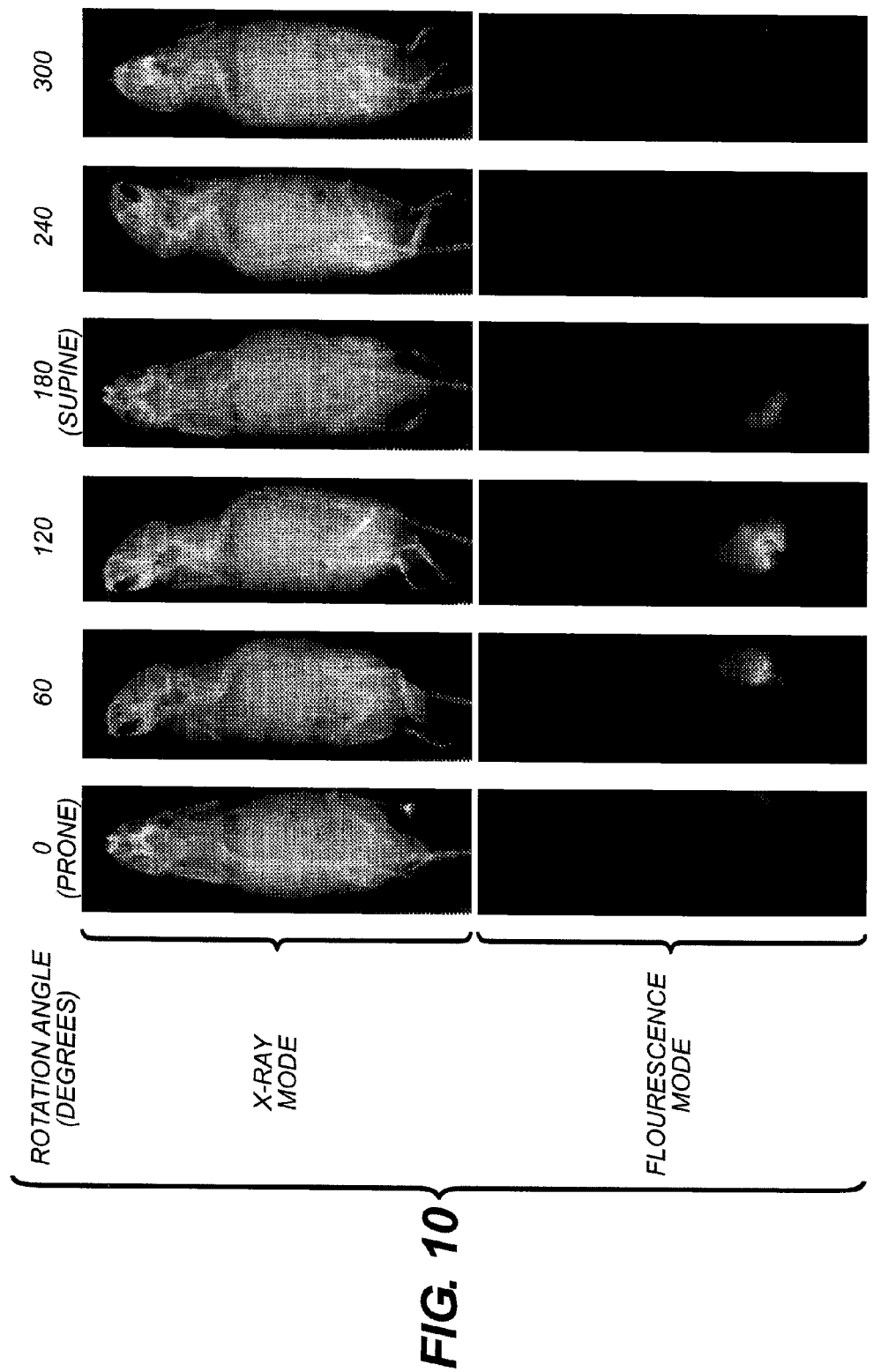
FIG. 10 shows six pairs of images, wherein each pair is comprised of an X-ray image and a fluorescence image, of a mouse in various postures achieved from crandiocaudal rotation by torsional support apparatus of FIG. 2A.

FIG. 10 shows six pairs of images, wherein each pair is comprised, as shown, of an upper X-ray image and a lower fluorescence image of a mouse in various postures achieved from crandiocaudal rotation by torsional support apparatus 300. The mouse was advanced by a craniocaudal rotation angle of 60 degrees between each pair. The X-ray images clearly show the craniocaudal rotation of the mouse. The fluorescence images are of a subcutaneous injection of a fluorescent imaging agent. The fluorescence images change as the craniocaudal rotation angle advances due to the rotation of the localized fluorescent imaging agent around the craniocaudal axis of the mouse. When the localized fluorescent imaging agent is rotated to angles behind the mouse, it disappears from the image due to optical absorption by the mouse tissue. Because the signal is dependent upon the depth of tissue between the animal surface and the distributed fluorescent/luminescent content inside the animal through which the light must travel, and that depth of tissue is dependent upon the animal posture, the precise control of the craniocaudal rotation angle, and hence the view angle, provided by torsional support apparatus 300 enhances the quantitation of molecular signals.

Figure 11:
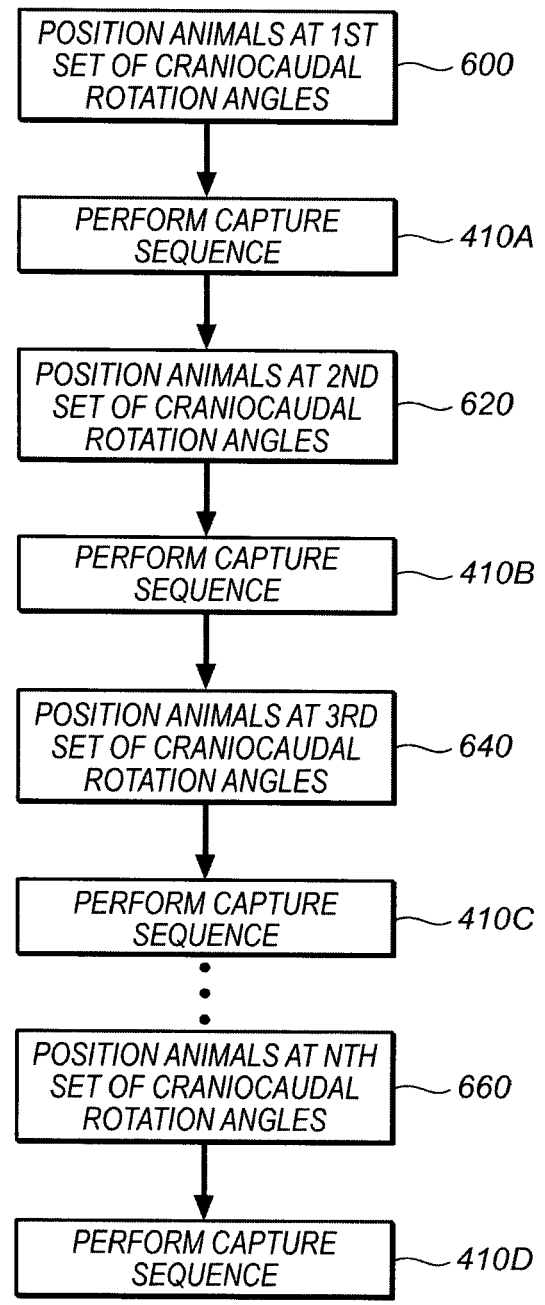
FIG. 11 shows a workflow diagram for craniocaudal rotation of a plurality of animals in accordance with a method of the present invention.
Figure 12A:
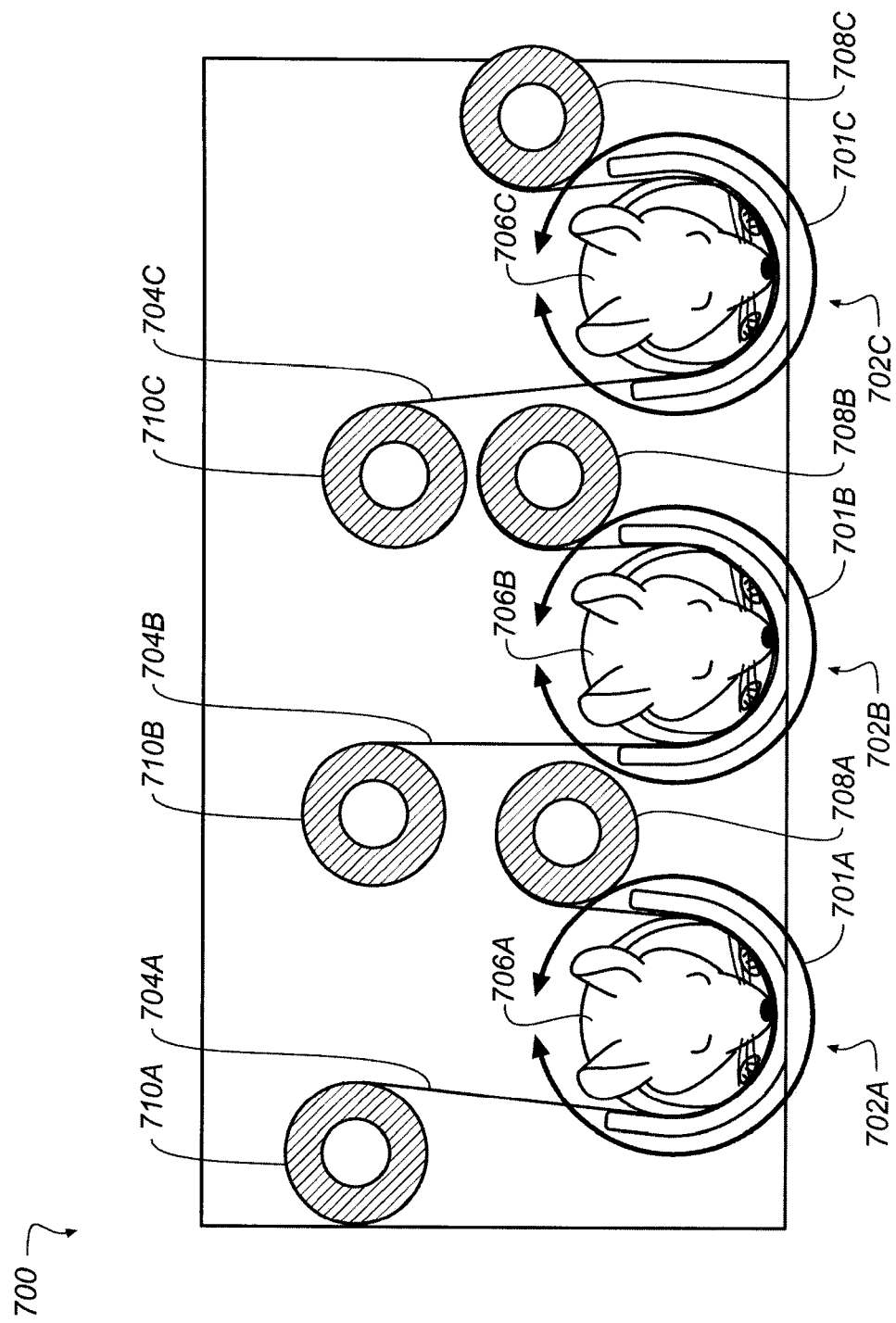
FIG. 12A shows a diagrammatic rear view of a multiple torsional support apparatus in accordance with the present invention.

FIG. 11 shows a workflow diagram for craniocaudal rotation of a plurality of animals 706A, 706B, 706C, shown in FIG. 12A in accordance with a method of the present invention. Because electronic imaging system 10 has a maximum field of view sufficiently large to image a plurality of animals, for example a maximum field of view of 200 millimeters×200 millimeters, steps 400, 420, 440, and 460 may simply be replaced by steps 600, 620, 640, and 660, wherein the craniocaudal rotation angle of each animal is independently controlled.

Figure 12C:
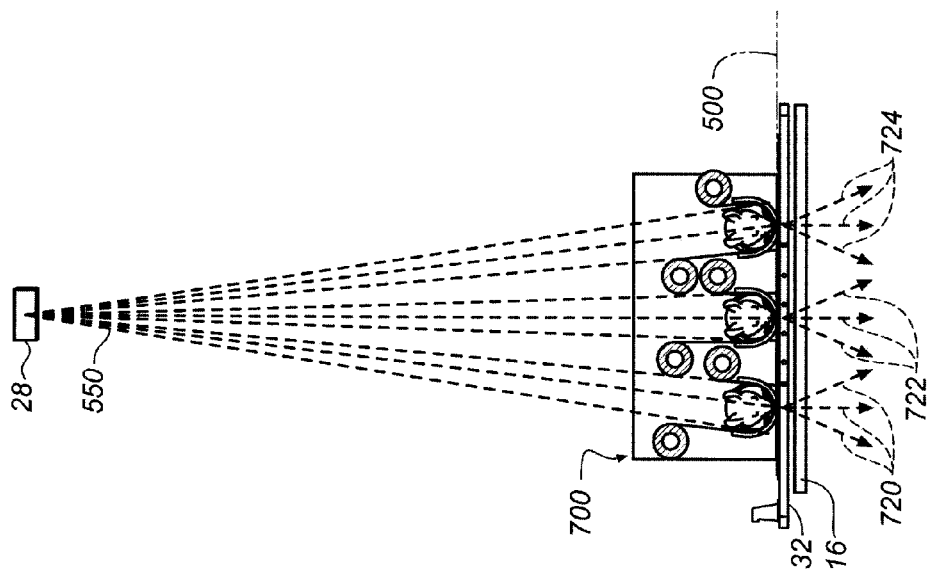
FIG. 12C shows a diagrammatic rear view of the multiple torsional support apparatus of FIG. 12A and removable high-resolution phosphor screen where the high-resolution phosphor screen has been installed and the animals are being imaged using an X-ray imaging mode.

FIGS. 12A-12C show multiple torsional support apparatus 700 in accordance with the present invention. Multiple torsional support apparatus 700 consists of three independent torsional support sections 702A, 702B, 702C. Middle torsional support section 702B includes an optically transparent flexible support film 704B and is shown to be essentially identical to torsional support apparatus 300. Middle torsional support section 702B supports an animal 706B and is horizontally positioned directly under microfocus X-ray source 28. Left and right torsional support sections 702A and 702C are slightly tilted toward middle section 702B so as not to obstruct X-rays emitted from microfocus X-ray source 28 from direct line-of-sight with animals 706A, 706C. Drive shafts 708A, 708B, 708C, 710A, 710B, and 710C are provided. Drive shaft 708A of left torsional support section 702A is positioned under drive shaft 710B of middle torsional support section 702B, and drive shaft 710C of right torsional support section 702C is positioned over drive shaft 708B of middle torsional support section 702B, so as to achieve a compact arrangement. The rounded bottoms of optically transparent flexible support films 740A, 740B and 740C are all tangent to focal plane 500, not shown in FIG. 12A. Independent stepper motors, not illustrated, are independently controlled by communication and computer control system 26, and independent belt drives, not illustrated, cause animals 706A, 706B, 706C to undergo independent craniocaudal rotations as indicated by arrows 712A, 712B, 712C. The compact arrangement of multiple torsional support apparatus 700 may be desirable for some applications in that it allows a high magnification of lens and camera system 26 but still includes the entire plurality of animals 706A, 706B, 706C within the field of view, hence achieving a high imaging resolution as desirable for analyzing animal models. Furthermore, the magnification of lens and camera system 26 may be increased further to zoom in on middle torsional support section 702B as desired.

FIG. 12B shows multiple torsional support apparatus 700 and removable high-resolution phosphor screen 32 where animals 706A, 706B, 706C have undergone independent craniocaudal rotation to prone postures during step 600, high-resolution phosphor screen 32 has not been moved beneath animals 706A, 706B, 706C and a molecular image set of animals 706A, 706B, 706C is being captured in step 412 by electronic imaging system 10 configured for an optical molecular imaging mode, as shown fluorescence mode. Excitation light of three different wavelengths 505A, 505B, 505C is sequentially projected by fiber optics 18 onto the ventral semigirths of animals 706A, 706B, 706C over their entire lengths, for configuration steps 470, 474, 476. Emission light 714A, 714B, 714C; 716A, 716B, 716C; and 718A, 718B, 718C is emitted from animals 706A, 706B, 706C, respectively; in fluorescent response to excitation light 505A, 505B, 505C and is captured in capture steps 472A, 472B, 472C by electronic imaging system 10 wherein lens and camera system 24 is focused on focal plane 500.

FIG. 12C shows support apparatus 700 when removable high-resolution phosphor screen 32 has been moved beneath animals 706A, 706B, 706C during step 414 and an X-ray anatomical image of the animals is being captured in step 416 by electronic imaging system 10 configured for X-ray mode. High-resolution phosphor sheet 34 is coplanar with focal plane 500. X-rays 550 are emitted by microfocus X-ray source 28 toward animals 706A, 706B, 706C and penetrate the animals depending upon the attenuation of the animals' soft and skeletal tissue. X-rays 550 then intercept high-resolution phosphor sheet 34 which responds by emitting a phosphorescent visible light 720, 722, 724 for animals 706A, 706B, 706C, respectively. Phosphorescent visible light 720, 722, 724 is captured in capture step 416 by electronic imaging system 10 wherein lens and camera system 24 is focused on focal plane 500. Animals 706A, 706B, 706C may undergo further independent craniocaudal rotation steps and electronic imaging system 10 may be repeatedly configured to capture molecular and X-ray images of the animals as desired, even through supine postures and all the way around and back to prone postures.

Figure 13A:
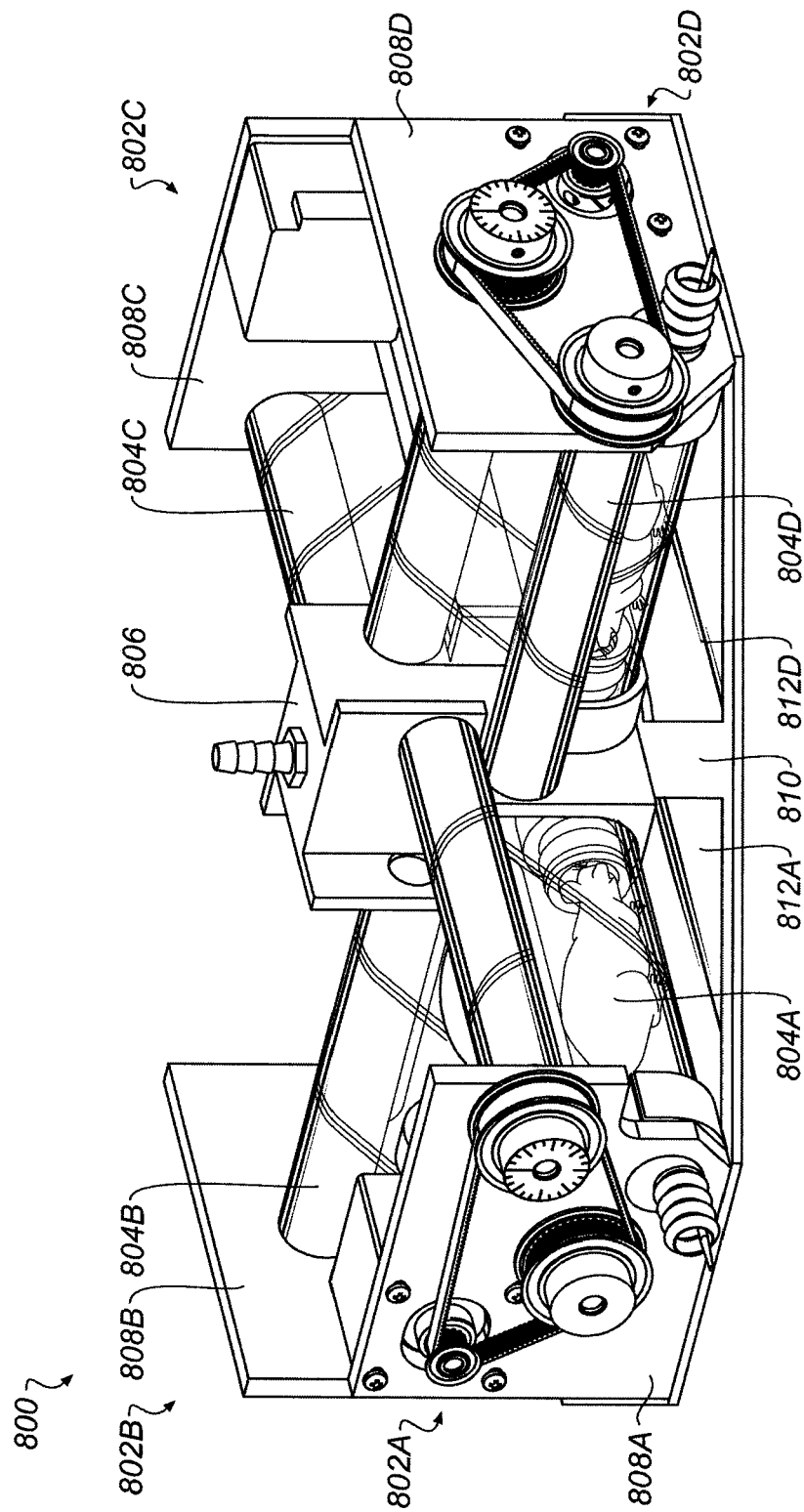
FIG. 13A shows a perspective view of another multiple torsional support apparatus in accordance with the present invention.
Figure 13B:
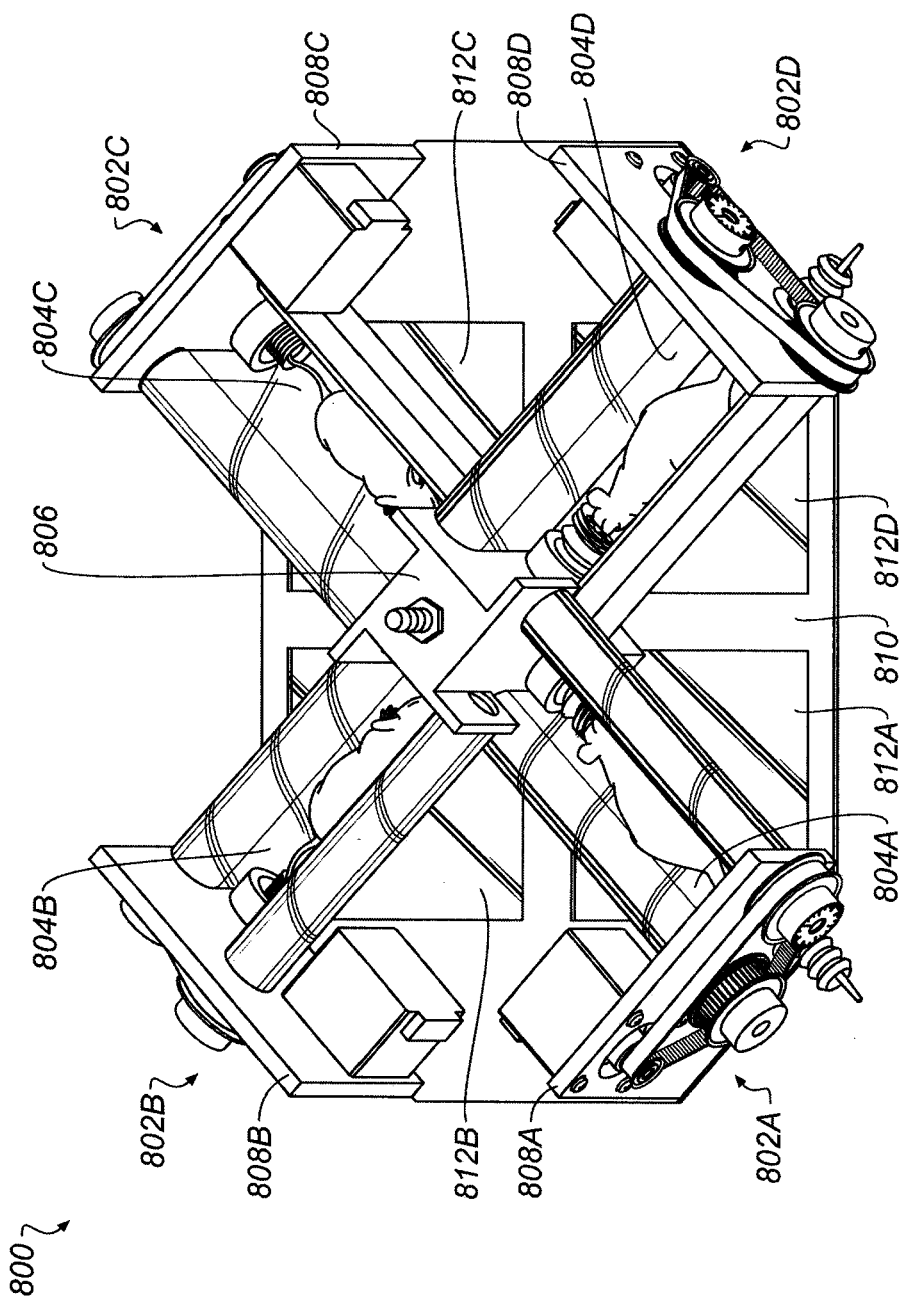
FIG. 13B shows another perspective view of the multiple torsional support apparatus of FIG. 13A.
Figure 13C:
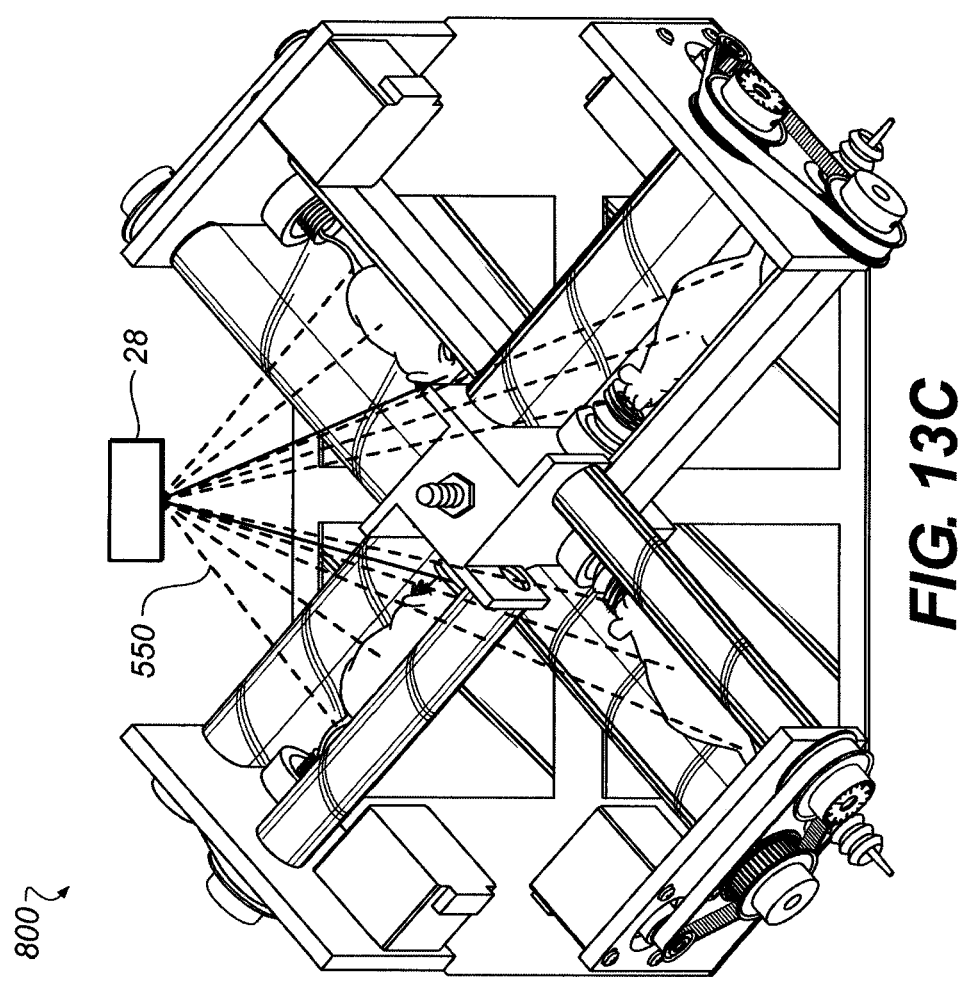
FIG. 13C shows a perspective view of the multiple torsional support apparatus of FIG. 13A where the animals are being imaged using an X-ray imaging mode.

FIGS. 13A-13C show another multiple torsional support apparatus 800 in accordance with the present invention. Multiple torsional support apparatus 800 comprises four independent torsional support sections 802A, 802B, 802C, 802C, each including a respective optically transparent flexible support film 804A, 804B, 804C, 804D arranged in a cross to provide a rotationally symmetric arrangement about the center of the cross. Those skilled in the art will appreciate that additional support sections could be included without departing from the invention. At the center of the cross is disposed a single anterior multiple bearing mount 806 which is positioned directly under microfocus X-ray source 28, and acts as a manifold in that it delivers inhalational anesthesia to all four sections. Spaced from mount 806 are located posterior bearing mounts 808A, 808B, 808C, 808C. A base plate 810 provides rigid mechanical coupling between anterior multiple bearing mount 806 and posterior bearing mounts 808A, 808B, 808C, 808D. Windows 812A, 812B, 812C, 812C are cut out of base plate 810. The first and second drive shafts within each section are offset vertically with respect to each other to allow the first drive shaft of any one section to be disposed above the proximal second drive shaft of the neighboring section, thereby allowing for a compact layout, i.e., a small footprint for anterior multiple bearing mount 806, of multiple torsional support apparatus 800. The rotationally symmetric layout of multiple torsional support apparatus 800 may be desirable for some applications in that the geometric magnification of the X-ray imaging, which is determined by the distance of the animal from the X-ray source, is rotationally symmetric.

Those skilled in the art will appreciate that the images acquired by the inventive apparatus and method may be employed in tomographic reconstruction of the contrast the animal presents in the corresponding imaging modes, such as X-ray mode, radioactive isotope mode, and optical imaging modes such as bright-field mode, fluorescence mode, luminescence mode.

Those skilled in the art will appreciate that the inventive apparatus and method are applicable to a photoacoustic modality wherein the torsional support apparatus 300 is suspended over a bowl in which an array of ultrasound sensors is disposed, the bowl has an optically transparent window in the bottom, in operation the bowl is filled with an optically transparent acoustic coupling medium, such as a liquid or gel, in acoustic contact with elongated, optically transparent, flexible support member or film 302, the animal is immobilized and placed in the upwardly open, U-shaped loop 304 in a recumbent posture, pulsed light is provided through the window to the animal, the light is absorbed by endogenous and/or exogenous material in the animal, the material releases energy as ultrasound, the ultrasound is detected by the array of sensors, and a electronic system performs a tomographic reconstruction based on the detected ultrasound. Because the penetration depth of the light is limited by absorption and scatter in the animal, the positioning of the animal in a variety of postures to access the various anatomical features of the animal is desirably enhanced by the improved control of the view angle enabled by the inventive apparatus and method to improve the experimenter's ability to quantify photoacoustic data. For example, photoacoustic calibrations that depend on the tissue depth, and hence the animal posture, may be more precisely determined. Also, different photoacoustic tomographic sections from a series of different view angles could be precisely stitched together given precise knowledge of the view angle.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

| | PARTS LIST |
|---|---|
| 10 | electronic imaging system |
| 12 | light source |
| 14 | sample environment |
| 16 | optically transparent platen |
| 18 | fiber optics |
| 20 | optical compartment |
| 22 | mirror |
| 24 | lens/camera system |
| 26 | communication/computer control system |
| 28 | microfocus X-ray source |
| 30 | optically transparent planar animal support member |
| 32 | high resolution phosphor screen |
| 34 | high resolution phosphor sheet |
| 36 | arrow showing movement of 34, 36 |
| 38 | access means or member |
| 40 | animal (mouse) |
| 42 | arrow |
| 300 | torsional support apparatus |
| 302 | elongated, optically transparent, flexible support member or film |
| 302a, 302b | longitudinal edges of 302 |
| 304 | upwardly open, U-shaped loop of 302 |
| 306 | recumbent animal in 304 |
| 308a, 308b, 308c | hoses |
| 310a, 310b, 310c | gas ports |
| 312a, 312b, 312c | hose barbs |
| 314 | belt drive |
| 316 | arrow |
| 318 | arrow |
| 320A, 320B | drive shafts |
| 324 | posterior bearing mount |
| 326 | anterior bearing mount |
| 328 | base plate |
| 330 | window |
| 332 | posterior hub |
| 334 | posterior guide |
| 336 | anterior hub |
| 338 | anterior guide |
| 340A, 340B | imaginary vertical planes |
| 342A, 342C, 342E | arrows showing rotation of 320A |
| 342B, 342D, 342F | arrows showing rotation of 320B |
| 344 | pulley for 320A |
| 346 | pulley for 320B |
| 348 | drive pulley |
| 350 | drive belt |
| 352 | stepper motor |
| 356 | set screw for 344 |
| 360 | cut-out |
| 364 | arrow showing movement of 306 into 304 |
| 368 | anterior expandable tubing segment |
| 400-478 | method steps |
| 500 | focal plane |
| 505A, 505B, 505C | excitation light |
| 510A, 510B, 510C | emission light |
| 511A, 511B, 511C | emission light |
| 512A, 512B, 512C | emission light |
| 550 | X-rays |
| 560 | phosphorescent visible light |
| 561 | phosphorescent visible light |
| 562 | phosphorescent visible light |
| 600-660 | method steps |

-continued

PARTS LIST

| | |
|---|---|
| 700 | multiple animal torsional support apparatus |
| 702A, 702B, 702C | torsional support sections |
| 704A, 704B, 704C | elongated, optically transparent, flexible support members or films |
| 706A, 706B, 706C | animals |
| 708A, 708B, 708C | drive shafts |
| 710A, 710B, 710C | drive shafts |
| 712A, 712B, 712C | arrows showing rotation of 706A, 706B, 706C |
| 714A, 714B, 714C | emission light |
| 716A, 716B, 718C | emission light |
| 718A, 718B, 718C | emission light |
| 720, 722, 724 | phosphorescent visible light |
| 800 | multiple animal torsional support apparatus |
| 802A, 802B, 802C, 802D | torsional support sections |
| 804A, 804B, 804C, 804D | support films |
| 806 | anterior multiple bearing mount |
| 808A, 808B, 808C, 808D | posterior bearing mounts |
| 810 | base plate |
| 812A, 812B, 812C, 812D | windows |

What is claimed is:

1. Apparatus for imaging an animal having a craniocaudal axis, comprising:
    an elongated flexible film for supporting such an animal in a position with its craniocaudal axis transverse to an axis of elongation of the elongated flexible film;
    a forming mechanism for limning the elongated flexible film into an upwardly open, U-shaped loop, the loop being sized for receiving and engaging such an animal;
    a moving mechanism for moving the elongated flexible film in a direction of the axis of elongation while maintaining the U-shaped loop, whereby movement of the elongated flexible film applies torsion to such an animal so that it is rotated about its craniocaudal axis; and
    an imaging system for imaging such an animal at various angles of craniocaudal rotation.

2. Apparatus according to claim 1, wherein the elongated flexible film is made from an optically transparent, flexible film.

3. Apparatus according to claim 1, wherein the forming mechanism for forming comprises:
    a pair of horizontally spaced, parallel drive shafts attached to the elongated flexible film at locations spaced along the axis of elongation; and
    a guide system for guiding the elongated flexible film to form the U-shaped loop between the drive shafts.

4. Apparatus according to claim 3, wherein the elongated flexible film has first and second longitudinally extending edges and the guide system comprises a pair of guides, one on each of the edges for forming the U-shaped loop.

5. Apparatus according to claim 4, wherein the U-shaped loop is tangent to a focal plane of the imaging system.

6. Apparatus according to claim 4, wherein the moving mechanism comprises a drive for rotating the drive shafts.

7. Apparatus according to claim 4, wherein each of the guides comprises a central passage, further comprising an opening on an upper side of the central passage of one guide for receiving a tail of such an animal and an anterior expandable tubing segment extending through the central passage of the other guide for engaging a head of such an animal.

8. Apparatus according to claim 7, further comprising a delivery system for introducing anesthesia into the anterior expandable tubing segment to anesthetize such an animal.

9. Apparatus according to claim 3, further comprising a base plate, mounting hub on the base plate for supporting the drive shafts and a window through the base plate through which light or radiation may pass toward the means for imaging.

10. Apparatus according to claim 9, wherein the imaging system comprises an X-ray source above the U-shaped loop and a phosphor screen movable beneath the window to receive radiation passing through such an animal in the U-shaped loop.

11. Apparatus according to claim 1, wherein there are a first plurality of elongated flexible films, a corresponding second plurality of forming mechanisms for forming, and a corresponding third plurality of moving mechanisms for moving, whereby a corresponding fourth plurality of such animals may be imaged.

12. Apparatus according to claim 11, wherein the pluralities are arranged side by side.

13. Apparatus according to claim 11, wherein the pluralities are arranged about a common center.

14. A method for imaging an animal having a craniocaudal axis, comprising:
    providing an elongated flexible film having an axis of elongation and longitudinally extending edges;
    forming the elongated flexible film into an upwardly open, U-shaped loop, the loop being sized for receiving and engaging the animal;
    supporting the animal in the U-shaped loop with the craniocaudal axis transverse to the axis of elongation;
    moving the elongated flexible film in a direction of the axis of elongation while maintaining the U-shaped loop, whereby torsion is applied to the animal so that it is rotated to various angles about the craniocaudal axis; and
    imaging the animal at various angles of craniocaudal rotation.

15. A method according to claim 14, wherein the elongated flexible film is made from an optically transparent, flexible film.

16. A method according to claim 14, wherein the U-shaped loop is tangent to a focal plane of the imaging.

17. A method according to claim 14, further comprising administering anesthesia to the animal supported in the U-shaped loop.

18. A method according to claim 14, further comprising guiding the longitudinal edges to maintain the U-shaped loop during movement of the elongated flexible film.

19. A method according to claim 14, wherein the imaging provides an X-ray image of the animal.

20. A method according to claim 14, wherein the imaging provides a radioactive isotope image of the animal.

21. A method according to claim 14, wherein the imaging provides an optical image of the animal.

22. A method according to claim 14, wherein the imaging provides X-ray and optical images of the animal for each angle of craniocaudal rotation.

23. A method according to claim 14, wherein the imaging provides radioactive isotope and optical images of the animal for each angle of craniocaudal rotation.

24. A method according to claim 14, wherein the imaging provides X-ray and radioactive isotope images of the animal for each angle of craniocaudal rotation.

25. A method according to claim 14, wherein the imaging provides X-ray, radioactive isotope, and optical images of the animal for each angle of craniocaudal rotation.

* * * * *

UNITED STATES PATENT AND TRADEMARK OFFICE
CERTIFICATE OF CORRECTION

| | | |
|---|---|---|
| PATENT NO. | : 8,660,631 B2 | Page 1 of 1 |
| APPLICATION NO. | : 12/475623 | |
| DATED | : February 25, 2014 | |
| INVENTOR(S) | : Feke et al. | |

It is certified that error appears in the above-identified patent and that said Letters Patent is hereby corrected as shown below:

In the Claims

Column 19
Line 27, please delete "limning" and insert --forming--

Signed and Sealed this
Thirteenth Day of May, 2014

Michelle K. Lee
*Deputy Director of the United States Patent and Trademark Office*